United States Patent
Alberts

(10) Patent No.: US 9,610,029 B2
(45) Date of Patent: Apr. 4, 2017

(54) SYSTEM AND METHOD TO FACILITATE ANALYSIS OF BRAIN INJURIES AND DISORDERS

(71) Applicant: THE CLEVELAND CLINIC FOUNDATION, Cleveland, OH (US)

(72) Inventor: Jay L. Alberts, Chagrin Falls, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

(21) Appl. No.: 13/644,371

(22) Filed: Oct. 4, 2012

(65) Prior Publication Data

US 2014/0100486 A1 Apr. 10, 2014

(51) Int. Cl.
A61B 5/11 (2006.01)

(52) U.S. Cl.
CPC ........... *A61B 5/1106* (2013.01); *A61B 5/1116* (2013.01); *A61B 5/1118* (2013.01); *A61B 2562/0219* (2013.01)

(58) Field of Classification Search
CPC ..... A61B 5/4528; A61B 5/103; A61B 5/1071; A61B 5/0053
USPC ............................ 33/511, 512; 600/587, 595
See application file for complete search history.

(56) References Cited

U.S. PATENT DOCUMENTS

| 5,984,475 A * | 11/1999 | Galiana et al. ............... 351/209 |
| 6,063,046 A * | 5/2000 | Allum .......................... 600/595 |
| 2006/0005846 A1* | 1/2006 | Krueger et al. ............. 128/898 |
| 2006/0015287 A1 | 1/2006 | Vock et al. |
| 2006/0241718 A1 | 10/2006 | Tyler et al. |
| 2008/0287821 A1 | 11/2008 | Jung et al. |
| 2009/0058660 A1* | 3/2009 | Torch .......................... 340/573.1 |
| 2009/0240172 A1* | 9/2009 | Fernandez Tournier et al. .............................. 600/595 |
| 2009/0306741 A1* | 12/2009 | Hogle et al. .................... 607/54 |
| 2009/0312817 A1* | 12/2009 | Hogle et al. .................... 607/54 |
| 2010/0198104 A1* | 8/2010 | Schubert et al. ............. 600/558 |
| 2011/0054356 A1* | 3/2011 | Merfeld ........................ 600/587 |
| 2011/0152711 A1 | 6/2011 | Santina et al. |
| 2011/0239026 A1 | 9/2011 | Kulik |
| 2012/0070044 A1* | 3/2012 | Avinash et al. ............... 382/128 |

(Continued)

FOREIGN PATENT DOCUMENTS

| JP | 11-225968 A | 8/1999 |
| JP | 2009-297501 A | 12/2009 |
| WO | 2011063248 A1 | 5/2011 |

OTHER PUBLICATIONS

PCT International Search Report, PCT/US2012/058628, mailed Mar. 13, 2013, pp. 1-11.

(Continued)

*Primary Examiner* — Daniel Cerioni
(74) *Attorney, Agent, or Firm* — Tarolli, Sundheim, Covell & Tummino LLP

(57) ABSTRACT

In an example embodiment, this disclosure provides a computer system that includes a processor configured to compute, based on test performance data of a user, at least one performance variable characterizing balance and postural stability, and at least one performance variable characterizing vestibulo-ocular reflex (VOR). For each performance variable, processor can compute a respective score based on the respective performance variable and based on a set of performance metrics. The at least one computed score can be output via an output device.

18 Claims, 32 Drawing Sheets

(56) References Cited

U.S. PATENT DOCUMENTS

2012/0330182 A1* 12/2012 Alberts et al. ................ 600/558
2013/0023787 A1*  1/2013 Dowd ........................... 600/558
2013/0268547 A1* 10/2013 Boroczky et al. ............ 707/758
2013/0315107 A1* 11/2013 Lindner .............. H04L 65/4061
                                                          370/277

OTHER PUBLICATIONS

The Extended European Search Report for Application No. 12838054.0, mailed Feb. 19, 2015, pp. 1-8.
Japanese Office Action dated Jul. 7, 2015, pp. 1-2.

* cited by examiner

INSTRUCTIONS

ON THE NEXT SCREEN, YOU WILL SEE THREE CIRCLES NUMBERED 1 THROUGH 3.

MOVE YOUR MOUSE TO CIRCLE NUMBER 1 (YOU DO NOT NEED TO "CLICK" ON THE CIRCLE).

WHEN YOU DO THIS, THE TEST WILL AUTOMATICALLY BEGIN.

MOVE YOUR MOUSE IN NUMERICAL ORDER, 1,2,3 JUST LIKE A "CONNECT THE DOTS" DRAWING, MAKING SURE YOU ENTER THE MIDDLE OF THE CIRCLE.

EACH TIME YOU ENTER A CIRCLE, THE CIRCLE WILL TURN GREY TO SHOW THAT YOU HAVE HIT THE CIRCLE.

IF THE CIRCLE DOES NOT TURN GREY, IT MEANS THAT YOU DID NOT ENTER THE CIRCLE COMPLETELY, OR YOU WENT IN THE WRONG ORDER.

IF THIS HAPPENS, FIND THE CIRCLE YOU ARE LOOKING FOR, AND DRAW TO IT NOW.

WHEN YOU HIT THE LAST CIRCLE, THE TEST WILL BE OVER.

YOU WILL COMPLETE THIS TASK FIVE TIMES, AND AFTER THE FINAL TIME, THE COMPUTER WILL TELL YOU THAT THE TASK IS COMPLETED.

[START THE TEST]

FIG. 8

INSTRUCTIONS

THIS NEXT TASK IS VERY SIMILAR TO THE ONE YOU JUST COMPLETED, BUT THERE WILL BE MORE NUMBERS.

YOU WILL SEE CIRCLES NUMBERED FROM 1 TO 25.

MOVE YOUR MOUSE TO CIRCLE NUMBER 1, AND THE TEST WILL AUTOMATICALLY BEGIN (JUST AS BEFORE).

FROM HERE, MOVE THE MOUSE TO THE NEXT NUMBER IN THE SERIES, ALL THE WAY UP TO NUMBER 25.

THIS TIME, THE CIRCLES WILL NOT GREY WHEN YOU HIT THEM.

YOU NEED TO MAKE SURE THAT YOU ARE GOING IN THE CORRECT ORDER BECAUSE YOU HAVE NO INDICATION OF IF YOU HIT THE RIGHT TARGET OR NOT.

ONCE YOU ENTER THE CIRCLE NUMBER 25, THE TEST WILL BE OVER.

YOU WILL ONLY TAKE THIS TEST ONCE.

[START THE TEST]

FIG. 14

INSTRUCTIONS

THIS NEXT TASK WILL HAVE BOTH NUMBERS AND LETTERS ON IT.

YOU WILL BE ASKED TO SWITCH BACK AND FORTH BETWEEN WHICH NUMBER CORRESPONDS TO WHICH LETTER OF THE ALPHABET.

FOR EXAMPLE, 1 GOES TO A, 2 TO B, 3 TO C, AND SO FORTH.

YOU WILL CONTINUE GOING THROUGH THE SERIES, FROM NUMBER TO LETTER UNTIL YOU REACH THE LAST NUMBER.

LIKE THE LAST TEST, THE CIRCLES WILL NOT GREY WHEN YOU HIT THEM.

YOU NEED TO MAKE SURE THAT YOU ARE GOING IN THE CORRECT ORDER BECAUSE YOU HAVE NO INDICATION OF IF YOU HIT THE RIGHT TARGET OR NOT.

ONCE YOU ENTER THE LAST CIRCLE, THE TEST WILL BE OVER.

THIS TEST WILL ALSO ONLY BE TAKEN ONCE.

[ START THE TEST ]

FIG. 17

SYSTEM AND METHOD TO FACILITATE ANALYSIS OF BRAIN INJURIES AND DISORDERS

CROSS-REFERENCE TO RELATED APPLICATIONS

This application claims the benefit of U.S. Provisional Application No. 61/542,548, filed Oct. 3, 2011, entitled SYSTEM AND METHOD FOR MOTOR AND COGNITIVE ANALYSIS, which is incorporated herein by reference in its entirety. This application also relates to U.S. Provisional Patent Application No. 61/262,662, filed Nov. 19, 2009, and PCT/US2010/057453, filed Nov. 19, 2010, the contents of each of which are hereby incorporated by reference in their entireties.

TECHNICAL FIELD

Inventions described herein relate generally to a system and method to facilitate analysis of brain injuries and disorders.

BACKGROUND

There are various neuromotor and neurocognitive disorders including Alzheimer's disease, Parkinson's Disease (PD), and progressive supranuclear palsy to name a few. Neuromotor and neurocognitive disorders affect motor function, cognitive function or both. Traumatic brain injuries are another category of condition that can affect motor function and cognitive function. These brain injuries can include mild traumatic brain injuries also common referred to as concussions, which can be graded on various scales.

In order to properly treat many neuromotor and neurocognitive disorders as well as brain injuries, it is desirable to better understand or classify an individual's condition. Accordingly, a variety of tests have been developed for various types of diseases and injuries. For example, one scale for assessing a patient's Parkinson's disease is the Unified Parkinson's Disease Rating Schedule (UPDRS). Various other tests exist that are utilized by a clinician to help the clinician categorize a patient's disorder.

To more efficiently administer and objectively analyze results of such tests, computerized systems for administering some of such tests have been proposed. U.S. Pat. No. 6,435,878 ("the '878 patent") proposes a system where a user's reaction time to a stimulus can be measured. However, the proposed system does not measure the quality of the user's interaction with the system. The system of the '878 patent also dynamically modifies a presentation time or quantity of a stimulus for the stimulus based on the user's performance, but does not qualitatively modify test difficulty based on user performance.

U.S. Pat. No. 7,294,107 ("the '107 patent") similarly refers to a testing system with which user reaction time can be measured. However, as with the '878 patent, the system does not measure the quality of the user's interaction with the system. The system of the '107 patent also determines based on user performance which tests to administer and whether to terminate a test, but does not qualitatively modify a particular test's difficulty based on user performance.

U.S. Pat. No. 6,517,480 ("the '480 patent") refers to a testing system in which a maze trace is detected and an overall time for completion of the test is detected, but the system does not provide for any qualitative measurement of the user's performance of the test or for modifying testing difficulty in view of user performance.

Moreover, none of the '878, '107, and '480 patents provide a system or method for time-based testing of a degree of cognitive ability, nor do they provide a system or method that presents data regarding a correlation of test results to patient information, such as medications the patient is taking and/or stimulation parameters used for Deep Brain Stimulation (DBS) of the patient.

SUMMARY

This invention relates to a system and method to facilitate analysis of brain injuries and disorders.

According to an example embodiment, a computer system can include a processor configured to compute, based on test performance data of a user, at least one performance variable characterizing balance and postural stability, and at least one performance variable characterizing vestibulo-ocular reflex (VOR). For each performance variable, processor can compute a respective score based on the respective performance variable and based on a set of performance metrics. The at least one computed score can be output via an output device.

In another example embodiment, a computer-implemented method can include computing, by a computer processor and based on test performance data of a user, at least one of a performance variable characterizing balance and postural stability and a performance variable characterizing vestibulo-ocular reflex (VOR). For each of the at least one performance variable, a respective score can be computed by the processor and based on the respective performance variable and based on a set of performance metrics. The processor can output, via an output device, the at least one computed score.

In still another example, a non-transitive computer-readable medium can store instructions executable by a processor, the instructions which, when executed by the processor, cause the processor to perform a method to assess an extent of a traumatic brain injury of a user. The method, corresponding to the instructions can include computing, based on test performance data of the user, at least one of a performance variable characterizing balance and postural stability, a performance variable characterizing cognitive functioning, a performance variable characterizing neuromotor functioning, and a performance variable characterizing vestibulo-ocular reflex (VOR). For each of the at least one performance variable, a respective score can be calculated based on the respective performance variable and based on a set of performance metrics. The at least one computed score can be output, via an output device, to facilitate diagnosing the traumatic brain injury of the user.

In some examples, the measurements may relate to functions affected by traumatic brain injuries, such as mild traumatic brain injuries (e.g., usually referred to as concussions). These types of traumatic brain injuries can be graded on various scales to indicate the severity. For the example of analyzing concussion-type injuries or other diseases, such as Parkinson's disease, balance and postural stability and/or vestibular functions may be tested in addition to neuromotor and cognitive functions. This invention also relates to systems and methods for displaying information derived from the underlying measurements. Such analysis and/or resulting display can help a physician or other health care provider diagnose the patient's condition.

In other examples, this invention also relates to systems and methods for detecting intentional underperformance and anticipatory responses of a patient during testing. This invention also relates to systems and methods for determining postural stability.

Example embodiments of the invention relate to a system and method that display information derived from measurements of vestibular, balance and postural stability function. In some examples, the information may be displayed as a spider graph having a plurality of vertices, each vertex corresponding to a score or index value. Each score/index value may be derived from a measurement of postural stability and vestibulo-ocular reflex (VOR) integrity.

Example embodiments of the invention relate to a system and method of determining whether a patient is intentionally underperforming or anticipating a correct response during testing.

Example embodiments of the invention relate to a system and method of determining postural stability using a combination of gyroscope and accelerometer measurements.

To facilitate use and access, one or more tests can be implemented as an Internet-based application that can be accessed by an authorized user at a remote location via a predetermined resource locator (e.g., a URL). Additionally, by implementing the system as a web-based application, test data can be maintained (anonymously) for a plurality of patients at a central server to facilitate further analysis and research. For example, results of the testing for a plurality of users further can be aggregated to generate a new index for classifying movement disorders or determining the severity of a movement disorder, which may (or may not) be correlated with existing standards, such as the commonly used Unified Parkinson's Disease Rating Scale (UPDRS).

In an example method, the display device can be part of a patient terminal (e.g., a handheld device), the measurement data is recorded at a server coupled to the patient terminal via a network, and the test result information is output at a clinician terminal coupled to the server via the network. In some examples, the network includes the Internet.

The various methods and system components disclosed herein may be practiced and provided, each alone, or in various combinations.

An example embodiment of the invention is directed to one or more processors, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The one or more processors may be embodied in a server or user terminal(s) or combination thereof. The user terminal may be embodied, for example, as a desktop, laptop, hand-held device, Personal Digital Assistant (PDA), television set-top Internet appliance, mobile telephone, smart phone, etc., or as a combination of one or more thereof. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the invention is directed to a hardware computer-readable medium, e.g., as described above, having stored thereon instructions executable by a processor to perform the methods described herein, and/or for storing output data produced via execution of the methods described herein.

An example embodiment of the invention is directed to a method, e.g., of a hardware component or machine, of transmitting instructions executable by a processor to perform the methods described herein.

BRIEF DESCRIPTION OF THE DRAWINGS

FIG. 8 depicts a screen shot GUI that can be utilized for providing instructions for a "seven's test", according to an example embodiment of the invention.

FIG. 14 depicts a screen shot GUI that can be utilized for providing instructions for a computer-implemented trail making test (Part A), according to an example embodiment of the invention.

FIG. 17 depicts a screen shot GUI that can be utilized for providing instructions for a computer-implemented trail making test (Part B), according to an example embodiment of the invention.

DETAILED DESCRIPTION

Figure 1:
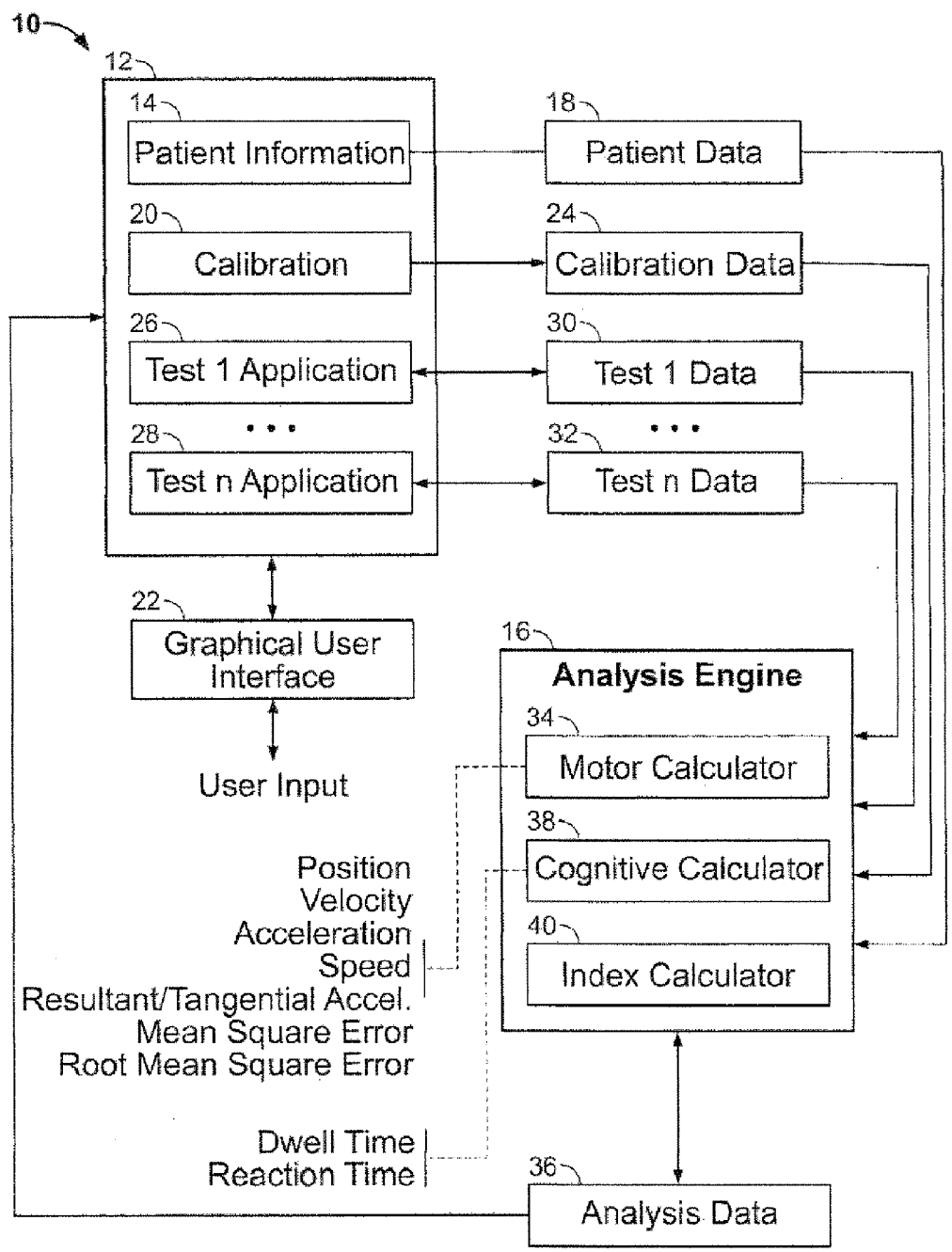
FIG. 1 is a block diagram of a test and analysis system, according to an example embodiment of the invention.

FIG. 1 depicts an example of a test system 10 that can be implemented according to an aspect of the invention. The system 10 includes a test engine 12 that includes methods and functions that are utilized to acquire data relevant to the testing process performed by the system 10. In an example embodiment, the test engine 12 may be located at a server to which a user computing device may connect to remotely access the methods and functions of the test engine 12.

The test engine 12, for example, can include a patient information module 14. The patient information module 14 can be programmed to acquire patient information that can be provided to an analysis engine 16 in the form of patient data 18. The patient information can include a series of templates or forms (e.g., an XML or other document) that can be completed by a user using an appropriate user input device, such as a keyboard and/or mouse and/or stylus. Examples of patient information include log-in information to authenticate the user with the system, such as a log-in ID and password. The patient information can also include information about a patient's current health condition as well as information about the environment in which the patient is taking the test. Additional information can be acquired relating to medication that the patient is currently taking, including names of medication, dosage, number of times per day, and the time since the last dosage. Those skilled in the art will appreciate various types of forms and constructs that can be utilized to acquire and send the patient data 18 to the analysis engine 16.

The test engine 12 also includes a calibration module 20 that is programmed to calibrate the system such as for remote operation in which specifics of the users' test equipment may be unknown. The calibration component 20, for example can be utilized to ascertain a relative two-dimensional size of a display or monitor on which the test is being implemented. For example, a graded scale can be graphically rendered onto a display, such as a series of spaced apart lines that are provided with a corresponding normalized scale known to the programmer. An article can be provided to the user of a known size (e.g., an 8½"×11" sheet of paper, a dollar bill, or credit card), which can be positioned adjacent to the scale by the user to ascertain dimensions (e.g., in both the x and y directions) of the user's display according to size of the image being displayed to the user via the graphical user interface 22. A user can in turn enter the corresponding score into the system 10 as calibration data 24 that is utilized by the analysis engine 16. Thus, by knowing the relative display size for the user's computing device, appropriate geometry and position information can be obtained from the subsequent battery of tests to be performed. The analysis engine 16 can employ the calibration data 24 to scale the corresponding testing data consistent with the user's particular test environment (e.g., display screen) on which the user is taking the test. Specifically, the data presented to the user for the test and/or the test results may be scaled according to the calibration data. For example, accuracy (i.e., size) of displayed targets and/or distances between displayed targets may be modified according to Fitts' law in accordance with the user's test environment.

In an alternative example embodiment of the invention, the calibration may be performed by transmitting data for presentation of three or four targets in the user's screen, one target at each corner of the screen. The system may record a number of pixels or defined X,Y positions between the targets as a representation of vertical and horizontal distances between the targets, which distances may be used as calibration data for scaling test data.

Alternatively or additionally, certain patient devices can be pre-configured having known configurations, such that calibration may be omitted. For example, devices having a predetermined configuration may be registered with the system. For instance, such preregistered devices or terminals can reside at doctors' offices, at hospitals, or other institutions.

In an alternative example embodiment, differences in the display screens may be ignored, and the test data presented to the user and the test result may be uniform across the various test platforms.

The test engine 12 also includes a plurality of test applications (e.g., functions or methods) 26 and 28, indicated as TEST 1 application through TEST N application, where N is a positive integer denoting any number of tests. Each test application can be programmed in a manner to test motor and/or cognitive functions, and/or a combination of motor and cognitive functions, of a user.

For example, the test can be similar to known tests such as a "Seven's test" (described in detail below with respect to FIGS. 9 and 10), a trail making test such as the trail making test parts A and B, a clock drawing test, and a reaction-time and motor task that can be utilized to test appropriate motor and/or neurocognitive functions of the user. Other tests with which the test engine 12 maybe programmed may include a center-out test (which assesses information processing speed (e.g., deciding to which target to move) and motor performance (e.g., quality of movement to a given target)), an Archimedes spiral test (to assess tremor in Parkinson's patients, where, as the patient progresses outward, tremor intends to increase), Benton's judgment of line orientation test (which measures visuospatial judgment in brain-injured patients), and tests whose complete renderings are dynamically provided as the user takes the tests. For example, a cyclical tracking test may be provided, for which a pattern for the user to trace is provided that includes points rendered after the user begins to trace the pattern. For example, a sine wave, circle, or other pattern, which changes or moves as the user traces the pattern may be displayed.

Each test application 26 to 28 can be provided to a user computer in an interactive manner that provides interactive graphical objects in the GUI 22, within a hardware display device, such as a computer or tablet screen. Such interactivity can be implemented through the use of an action script or other functions or methods that can be provided to the user, some of which can vary according to the platform in which the test engine 12 is being implemented, for example, based on a calibration as described above.

In an example embodiment, the test engine 12 can be implemented using the Flash platform, such as can be programmed using ADOBE® FLEX® software available from Adobe Systems Incorporated. The Flash platform has advantages in that, for example, it has an extremely high market penetration and no additional software components are required to be installed on the user's machine, such as when the test engine 12 is accessed remotely such as via a web browser of the user's machine. Advantageously, the FLEX® applications for each of the components of the applications or methods 14, 20, 26 and 28 may provide a stateful client where changes can occur on the display without requiring to load a new web page. Additionally, it has been determined that such an implementation allows sufficient resolution of geometry and position data to be acquired such that corresponding test results can be analyzed to provide meaningful information about motor, cognitive and cognitive-motor function of the user.

Data is acquired for each test application 26 to 28 as corresponding respective test data 30 to 32, which can be provided to and/or utilized by the analysis engine 16. Thus, by performing a plurality of multi-part tests 26 through 28, each test can provide corresponding test data 30 to 32 that can be analyzed by the analysis engine 16 to provide meaningful information and results based on the test data 30 to 32.

The test data can include an indication of which test of a plurality of different tests is being performed along with an indication of the position of graphical objects (e.g., targets) for the test as well as an indication of the position for a cursor or other pointing device that is utilized for performing the test. For example, the test application 26 to 28 can employ a get_cursor_pos( ) or other Application Programming Interface (API) to monitor and obtain cursor position information that is stored along with temporal information, such as the times corresponding to the obtained cursor positions, as the test data 30 to 32. The sampling of such data may be at a rate of, for example, 30 Hz.

As an example, a test application 26, 28 can display on the display a GUI having one or more targets, each as a graphical object having a shape (e.g., a circle, oval, triangle or rectangle) that encompasses or bounds a set of coordinates on the user's display device. A user can position on the display a cursor or other graphical object having its own object position in two-dimensional space (e.g., having X and Y coordinates), for example, using a pointing device, such as a mouse or stylus for touch screen, or without a pointing device, such as via a finger on a touch screen. The test application 26, 28 can provide instructions requesting the user to position the cursor/object or draw lines between two or more particular targets. The movement of the cursor on the screen relative to the known position of each of the targets (corresponding to the test data 30 to 32) can be analyzed by the analysis engine 16.

The analysis engine 16 may include, for example, a motor calculator 34 and/or a cognitive calculator 38. The calculators 34 and/or 38 may be, for example, software modules stored on a computer-readable hardware device, which may be executed to perform various calculations based on the same or different input parameters.

In an example embodiment, the motor calculator 34 is programmed to determine a number of one or more kinematic variables based on the test data 30 to 32. For example, the motor calculator 34 can be programmed to determine a position of the cursor or pointer device, a velocity, an acceleration, a speed and/or a tangential acceleration for each sample of test data acquired during a test interval. For example, the tangential acceleration may be used by the analysis engine 16 as an indication of degree of curvature in user movements.

In an example embodiment, the motor calculator 34 can also determine derivative information of the above-referenced variables, such as corresponding to a measure of how close to the user's line between a pair of targets is fitted to an ideal straight line between the pair of targets. For example, for every data point residing on the ideal straight line between sequential targets, a distance to a corresponding point on the line drawn by the user can be determined. The sum of the determined distances between the respective points can be determined, and divided by the number of points for which the distances were determined to provide an average associated with the ideal line relative to that drawn by a user. This can be repeated for a line drawn by a user between respective targets to provide an objective indication of the accuracy of lines drawn.

In an example embodiment, the motor calculator 34 may further calculate a means square error by determining an average of the error squared for the difference between the ideal and actual lines. In an example embodiment, the motor calculator 34 may further calculate the root mean squared error or standard deviation of the difference between the ideal and actual lines, for example by calculating the square root of the means square error. Thus, the motor calculator 34 can determine various values representative of the average distance that the user's data points on the user's line deviate from the idea line.

In an example embodiment, average, means square error, root means square error, and/or standard deviation information may be similarly calculated for deviation, over the course of a test, per each recorded position, each separate X position and Y position, and/or on a per line basis, between speed, velocity, acceleration, tangential acceleration, etc., between actual recorded values and ideal values for those parameters.

Other information includes whether the user has drawn crossing lines, as described below with respect to FIGS. 15 and 16.

The above is not intended as an exhaustive list of calculations which the motor calculator 34 may perform, and other example embodiments provide for calculation of additional or alternative variables and parameters based on the acquired test data 30 to 32 that is sampled over time. The results of the calculations determined by the motor calculator 34 can be stored as part of analysis data 36. The analysis data 36 can also include calibration data 24 and patient data 18, which can be utilized to improve the accuracy of the calculations by the motor calculator 34 and the cognitive calculator 38. Alternatively, calibration data may be used, as described above, to alter the administered test, so that results of tests administered at different platforms are comparable, without requiring further consideration of differences between the platforms, e.g., as reflected by the calibration data 24.

In an example embodiment of the invention, the cognitive calculator 38 is programmed to compute variables or parameters relevant to assessing cognitive function of a patient-user. For example, the cognitive calculator 38 can compute a dwell time based on the acquired test data 30 and 32. A dwell time can correspond to a time period during which a cursor or other graphical object is within a given predefined bounded area, such as can be defined as an X and Y position or range that encompasses a displayed graphical object or target. The computed dwell time may be used to assess a patient's set switching ability, to refocus attention from one task to another, for example, where dwell time reflects a dwell period in a first target (after initial movement to the first target) before moving to the next target. Dwell time may be an indicator of "cognitive freezing" in neurocognitive or other patient groups. The cognitive calculator 38 can also calculate the reaction time, such as corresponding to a time interval between a presentation of a stimulus and the initiation of movement of a pointing device by a user during a reaction test application 26, 28, which can be further utilized by the cognitive calculator 38 to generate a score of the patient's information processing capacity. In an example embodiment of the invention, the cognitive calculator 38 may further use data output by the motor calculator 34, e.g., representative of motor function quality, to calculate data representative of cognitive ability.

For example, an initial speed or acceleration when leaving a given target to move to a following target may be used as a cognitive measurement in certain instances. For example, if the initial phase of movement is relatively rapid (with high velocity and acceleration), and the user moves to the correct target, this information may be used to conclude that the user movement was made primarily under predictive or feedforward control (i.e., the user was very sure of where to go). On the other hand, if the speed or acceleration is relatively low or there are multiple starts and stops once the user leaves the target, the information may be used to conclude that the patient is unsure of the target to which to move, indicative of a deficiency in information processing speed, especially where other components of the user movements are relatively normal or can be made relatively quickly. It should be understood and appreciated that certain types of calculations may not apply to different types of tests depending upon the main purpose of the test.

In an example embodiment of the invention, the analysis engine 16 can output results of calculations to provide corresponding analysis data 36. Thus, the analysis data 36 can include results data based upon the methods and calculations performed by the motor calculator 34 and/or the cognitive calculator 38 based on test data 30 to 32 acquired for each of the respective test applications.

In an example embodiment of the invention, the analysis engine 16 may include an index calculator 40 that is programmed to compute one or more indices based upon the output results determined by the motor calculator 34 and/or cognitive calculator 38 for a patient. For example, the index calculator 40 can aggregate the analysis data determined for a given set of test data acquired for a given patient to determine an index (or score) having a value indicative of motor function for the given patient based on the aggregate set of test data. Alternatively or additionally, the index calculator 40 can compute an index (or score) having a value indicative of cognitive function for a patient based upon the set of test data. Alternatively or additionally, the index calculator 40 can compute an index (or score) having a value indicative of cognitive-motor function for a patient based upon the set of test data. The index calculator 40 can be normalized according to a known scale or index, such as the UPDRS. Alternatively or additionally, the index calculator 40 can calculate a new scale that provides an indication of motor and/or neurocognitive functions for the patient. The resulting output for the index calculation can be provided and stored as part of the analysis data 36 for subsequent analysis, e.g., by a clinician who may access the stored analysis data 36.

In an example embodiment of the invention, the system may modify factors used for the index calculation based on the corpus of data for a plurality of patients. For example, if a large number of users who are considered generally healthy perform poorly on a certain test, the test results for that test may be modified by a low weighting factor.

In an example embodiment of the invention, as a user takes one or more tests, the system may generate analysis data 36 which indicates that the test(s) presented to the user are too difficult or too easy for the user. For example, where calculated scores are extremely low, the scores may indicate that the user is below a certain threshold level of ability, but do not finely indicate the user's level of ability below that certain threshold. Similarly, where calculated scores are extremely high, the scores may indicate that the user's level of ability is above a certain threshold level of ability, but do not finely indicate the user's level of ability above that certain threshold.

Accordingly, in an example embodiment of the invention, the test engine 12 further includes a module for accessing stored analysis data concerning a current patient and selecting one of the TEST applications 1-N to next output to the user based on past performance indicated by the accessed analysis data. For example, where the test engine 12 determines from the analysis data that the user's performance is below a predetermined threshold, the test engine 12 may select a next test that is ranked as being at a particular low difficulty level. For example, difficulty may be ranked according to target accuracy (i.e., the size of the displayed targets (e.g., relative to calibrated screen size)) and/or distance between the displayed targets (e.g., relative to calibrated screen size). For example, a test having targets at a first distance from each other and of a first size may be ranked as easier than another test of the same type having targets that are at a second distance from each other, longer than the first distance, and/or that are of a second size, smaller than the first size. In an example embodiment, the change in test difficulty may be implemented by re-administering the same type of test as a previously administered test, with changes to the target accuracy and distances and thus changes in the difficulty level of the re-administered test.

In an alternative example embodiment, the change in test difficulty may be implemented by re-administering the same test or same type of test as a previously administered test, but with changes to the moving status of at least one target. For example, an increase in difficulty may involve changing from a stationary target to a moving target, or changing from a slow-moving target to a faster target. Similarly, a decrease in difficulty may involve changing from a moving target to a stationary target, or changing from a fast-moving target to a slower target. Difficulty may be ranked according to moving status.

In an alternative example embodiment, the change in test difficulty may be implemented by selecting a different type of test, which test type is ranked at a different difficulty level than that of a previously administered test.

In an example embodiment of the invention, during administration of a test, the analysis engine 16 may produce part of the analysis data 36 associated with the test, even before completion of the test. During the test, the test engine 12 may access the partial analysis data 36 produced for the test prior to its completion, and may modify the current test during its administration based on the partial analysis data 36. For example, during the administration of the test, the test engine 12 may enlarge previously displayed targets of the test and/or shorten the distance between the previously displayed targets and/or change targets between moving and stationary states. Alternatively or additionally, where the test dynamically displays targets during its administration, the test engine 12 may display new targets that are larger than those previously displayed, or at distances that are shorter than the distances between pairs of previously displayed targets, or having a different moving status compared to previously displayed targets.

Figure 2:
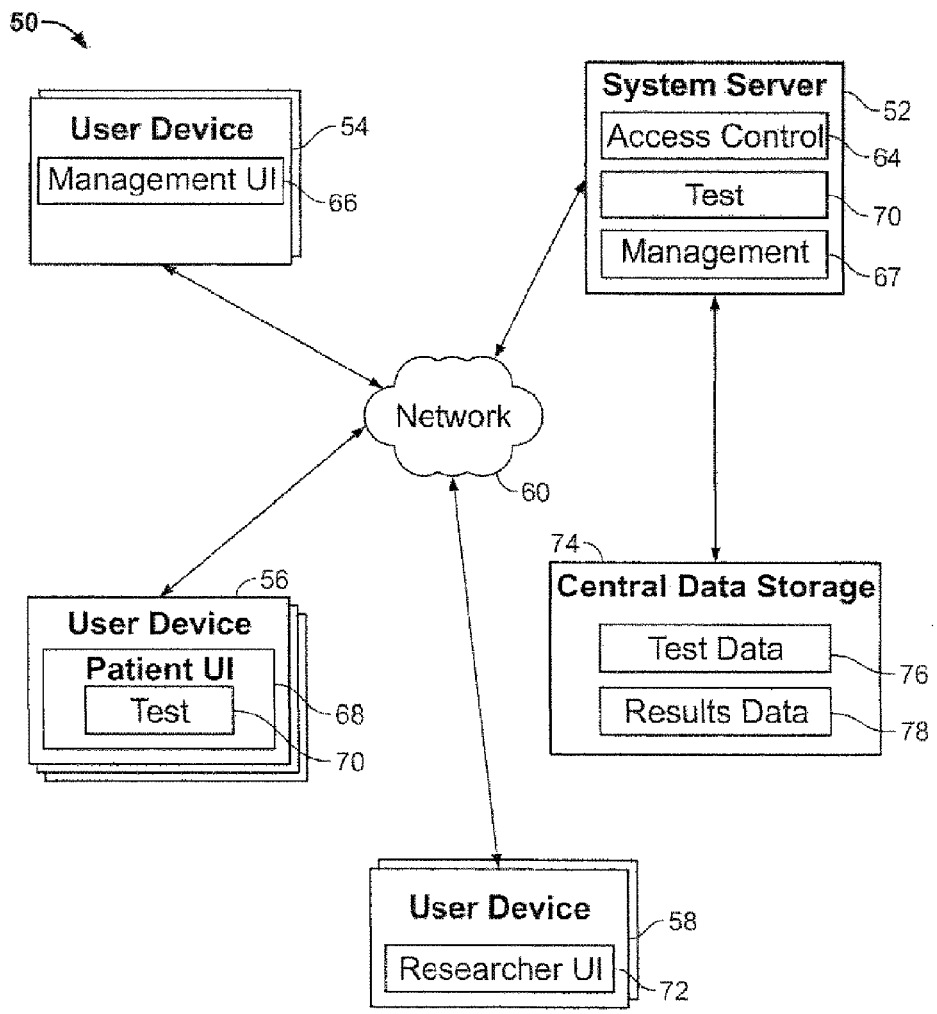
FIG. 2 depicts a system architecture that can be implemented for testing and analysis of motor and cognitive functions, according to an example embodiment of the invention.

FIG. 2 depicts an example of a network system 50, including an example architecture for performing testing, analysis and/or evaluation. In the example of FIG. 2, the system 50 includes a system server 52 that is programmed to provide methods and functions for use to implement various methods remotely at user devices indicated at 54, 56 and 58. Each of the user devices 54, 56 and 58 is connected to or can communicate with the system server 52 via a network 60. The network 60 may include a local area network (LAN), wide area network (WAN) (e.g., the Internet) or a combination of networks, including private and public domains, as is known in the art.

In an example embodiment, the system server 52 may include a web server having a plurality of different functions and methods, each of which can be accessed via a corresponding resource locator, such as a uniform resource location (URL). In an example, the system server 52 includes an access control function 64 that provides a level of security such that only authorized users can access various other functions and methods of the system. The access control function 64 can provide a log-in user interface screen to each of the user devices 54, 56 and 58, which can require a user ID and password for each user for authentication. Each user ID and password can be associated with a corresponding level of authorization to selectively provide access to one or more of the other functions and methods to be provided by the server system 52. While FIG. 2 illustrates devices 54, 56, and 58 as separate devices, the operations of each may be performed on a single device, but may be logically separated according to the log-in information. In an example embodiment, a single set of log-in information may provide authorization for access to operations of more than one of the shown devices 54, 56, and 58.

Figure 26:
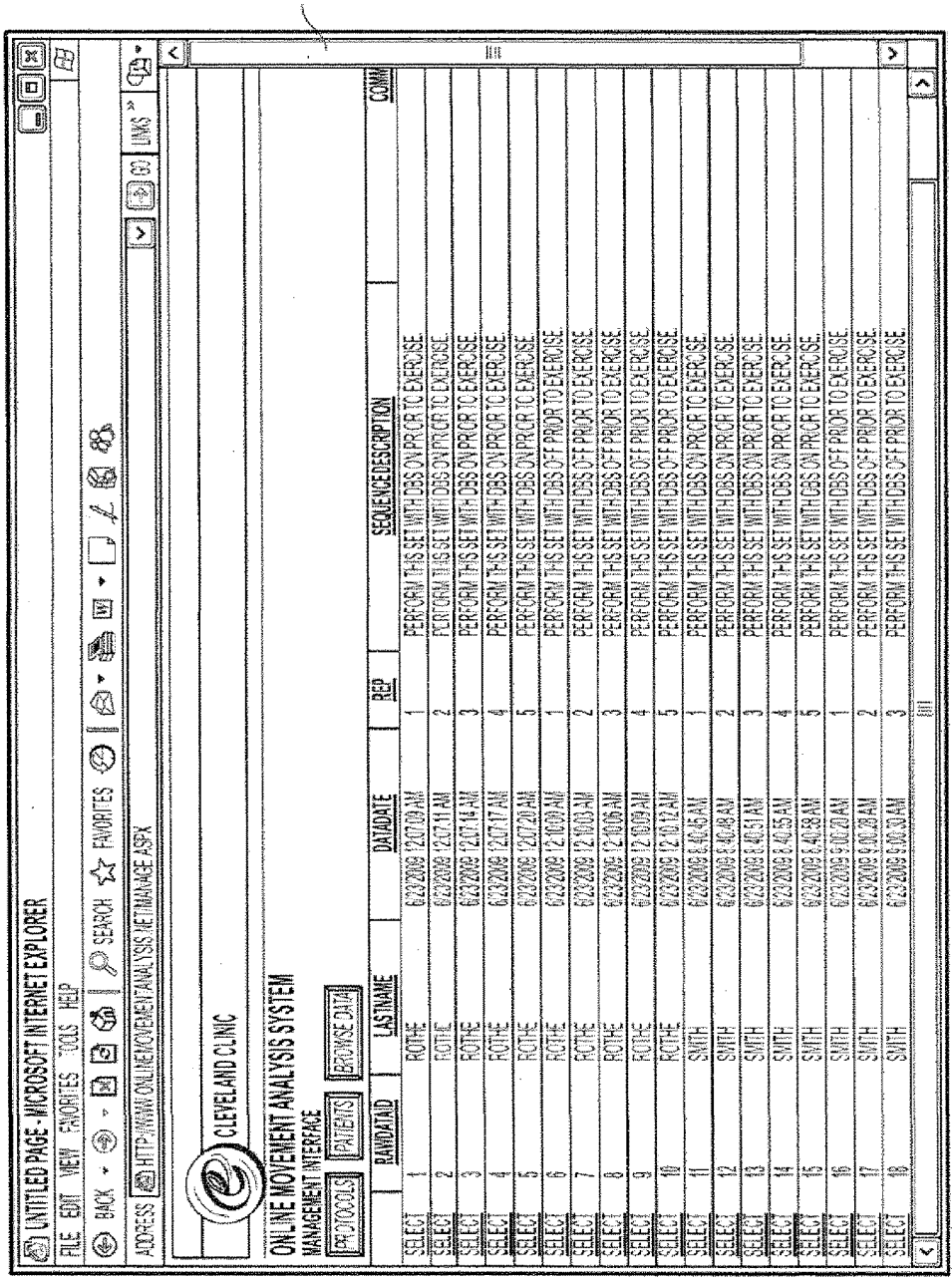
FIG. 26 depicts a screen shot for another management user interface that can be utilized for browsing and selecting patient test data, according to an example embodiment of the invention.
Figure 27:
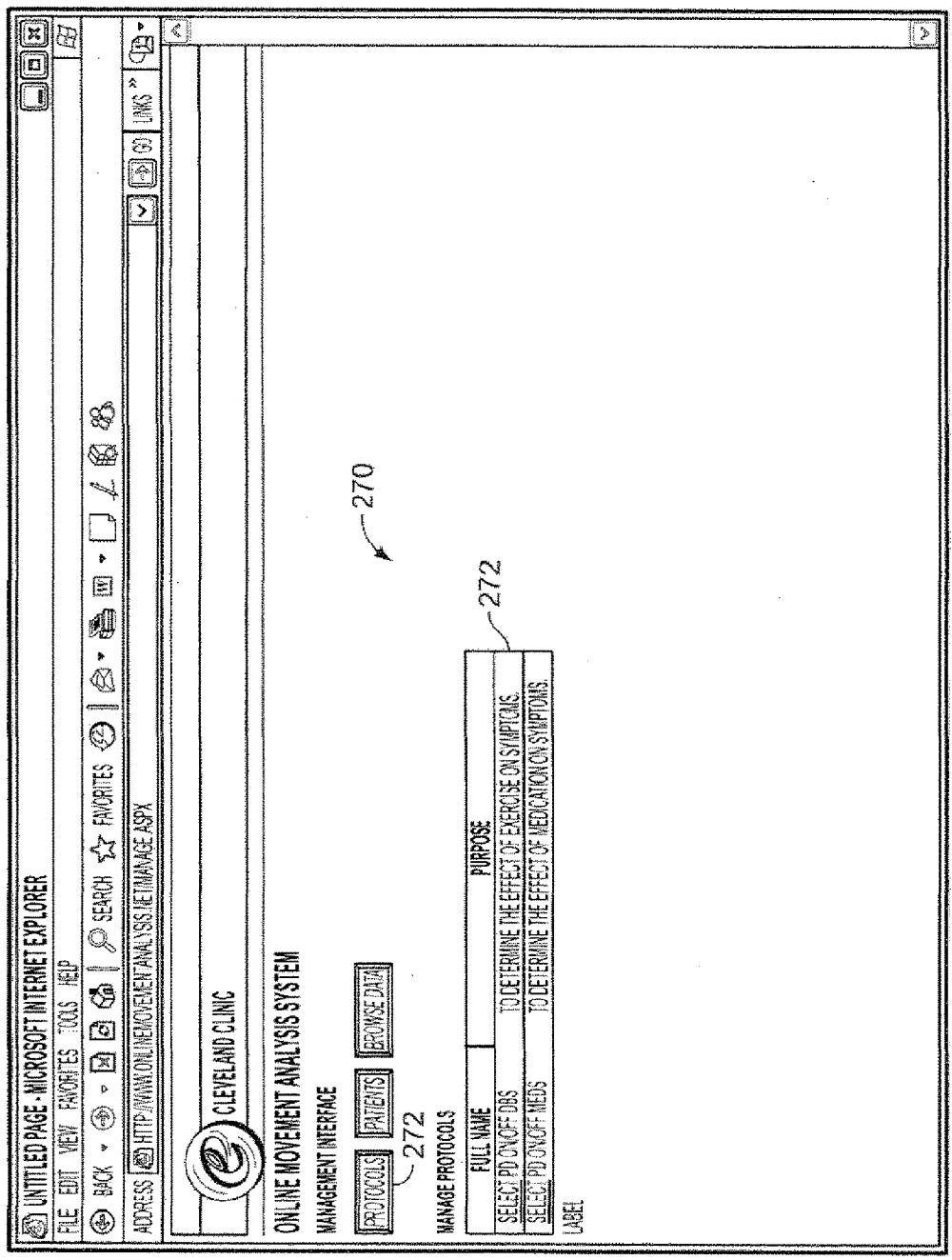
FIG. 27 depicts another management user interface that can be utilized for managing patient protocols employed during testing, according to an example embodiment of the invention.

For example, the user device 54 can be assigned a high or unlimited authorization level and utilized to provide one or more management user interfaces 66, for accessing each of the functions and methods provided by the server system 52, including accessing corresponding management functions and methods indicated schematically at 67. Thus, the authorized user of the management user interface 66 can access various management functions 67 for the patient information, browsing test data and the like. For example, the user interface 66 may be a clinician interface via which a clinician may access test results for tests taken by the clinician's patients or other related information. Examples of selected management user interface screens are shown in FIGS. 26 and 27.

The user device 56 can include a patient user interface 68 that can provide a limited amount of access such as to the testing functions and methods 70. For example, after logging in via the access control function 64, a patient user interface 68 can be used to access the test applications 70, which can be graphically displayed in the patient GUI. The test applications can be provided as interactive web pages programmed with functions and methods for performing various tests and obtaining patient-controlled movement information from the patient-user.

The test methods 70 that are provided to the patient user device 56 via the patient user interface can be implemented using ADOBE® FLEX® or another similar software or platform having a high market penetration. By having a sufficiently high market penetration, substantially no software needs to be installed or loaded onto an individual user's device. In response to interaction with the tests provided via the test methods 70, test data 30 to 32 may be obtained by the system server 52 for storage in a central data storage 74 (described in further detail below). Methods of the analysis engine 16 may be performed locally at the patient user device 56 or remotely at the system server 52.

Examples of associated graphical user interfaces associated with the testing functions and methods that can be presented to the user are shown and described herein with respect to FIGS. 4-20.

Another user device 58 can include a research user interface 72 that provides access to relevant data (e.g., excluding patient identifying information) such as to facilitate research and analysis of the test data. For example, a researcher or other authorized user can access a set of test data for a plurality of patients and, in turn, perform statistical methods or other mathematical operations on the set of data to ascertain relevant information, such as correlations or likelihoods. A researcher might also utilize the analysis data to draw correlations between other information entered by the user (e.g., patient data, including an identification of medications, dosage and the like) relative to test results for each of a plurality of users. Such analysis can provide information that can be stored in the central data storage 74 for subsequent usage and review by other authorized users.

For example, correlations can be drawn between medication and test results and changes in test results over time, which correlations can be presented to a physician or other authorized user via the management user interface 66.

Alternatively or additionally, certain patient devices can be preconfigured having a preset authorization status, such that authorization would not be required. Such devices known to the system server 52 can access the system server 52 through the network 60 or through a secure local area network or other suitable connection. For instance, such preconfigured terminals can reside at doctors' offices, hospitals or other institutions.

In an example embodiment, regardless of the configuration and distribution of patient user devices 56, the test data is consolidated into a database or other central data storage 74 that is associated with the central system server 52.

The central data storage 74 can include raw test data 76 and results data 78. While central storage 74 is shown as a single storage device and/or logical storage location, in an example embodiment, the raw test data 76 may be stored separate from the results data 78, e.g., for quicker response time to results data queries.

The raw test data 76 and results data 78 can be indexed by patient and by individual test as well as include patient specific information (in an example embodiment, excluding patient identifying information other than perhaps a patient unique identify number) for purposes of separating the patient data from one patient from that of another patient. As described herein, the test methods 70 and the system server 52 can be programmed to perform calculations on the raw test data acquired from a patient user interface via the testing application being implemented thereon.

Similarities between patients residing in a given cluster (i.e., patients who share certain characteristics) can be utilized to facilitate treatment and diagnosis of other patient's having similar conditions. For example, a clinician may enter information (e.g., patient information with respect to medication (type and/or dosage), stimulation parameters (e.g., of a DBS therapy), symptoms, conditions, and/or diagnoses) via the management user interface 66, which can be tagged (or programmatically linked) to the test data and results data of the patient, such as to augment or provide metadata that can be further evaluated or considered to facilitate clustering of patients and understanding the respective conditions. In this way, the test data for a more statistically significant population can be maintained for performing statistical analysis of test data, which can be mined or otherwise evaluated statistically or otherwise, e.g., via the researcher user interface, to understand the correlations of symptoms and conditions. For example, the system of the invention may be queryable for test result data by symptom(s) and/or diagnosis, in response to which the system may return results data 78 concerning those patients matching the symptom(s) and/or diagnosis, and/or averages and/or other aggregate data of the results data 78.

In an example embodiment, the system and method of the invention may provide for a clinician, using the user device 54, to input a proposed change, e.g., with respect to medication (type and/or dosage) and/or stimulation parameters (e.g., of a DBS therapy), for a particular patient for whom patient information and test results have been obtained. In response to a query triggered via user-selection of a command at the user device 54, the system server 52 may search the central data storage 74 for patients associated with patient data and test data similar (by a predetermined degree) to those of the particular patient. The server may further search for those of the patients who have been subjected to a change similar to that proposed for the particular patient and for whom subsequent test results data have been obtained. The server may output for display at the user device 54 an average of such subsequent test results, thereby indicating to the clinician an expected change in the particular patient's condition with the proposed change, measured in terms of expected change in test results.

Alternatively or additionally, the system may output a medical condition category corresponding to the average of such subsequent test results. For example, different intervals of test scores may be associated in memory with different categories of cognitive and/or motor skills. The category under which the average of the subsequent test results falls may be output. Alternatively or additionally, the expected direction of change to the medical condition classification may be output, e.g., whether the cognitive and/or motor skills are expected to improve or decline.

FIGS. 3 through 27 show example screen shots or other graphics for presentation in a user interface, to provide a general understanding of the algorithms and functionality that can be implemented by the systems 10 and 50 shown and described with respect to FIGS. 1 and 2.

Figure 3:
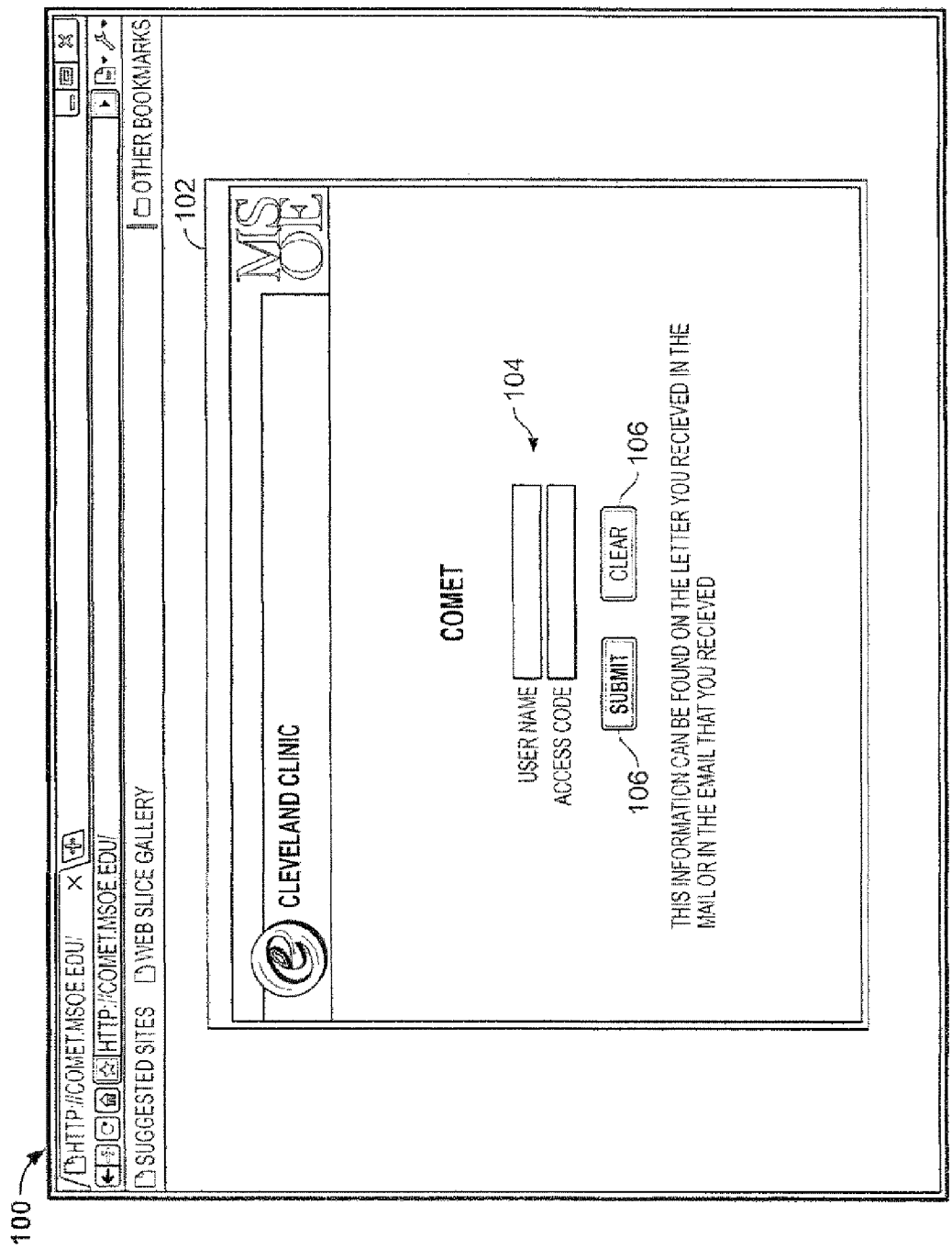
FIG. 3 is a screen shot for a log-in screen, according to an example embodiment of the invention.

FIG. 3 depicts an example of a screen shot 100 including a GUI element 102 that can be utilized for access control into the system, as described in detail above. The GUI element 102 includes user entry fields 104 that can be utilized for obtaining a user name and access code for authorized use of the system. Graphical buttons or others graphical interface elements 106 can be provided for submitting or clearing information with respect to the user entry fields 104.

Figure 4:
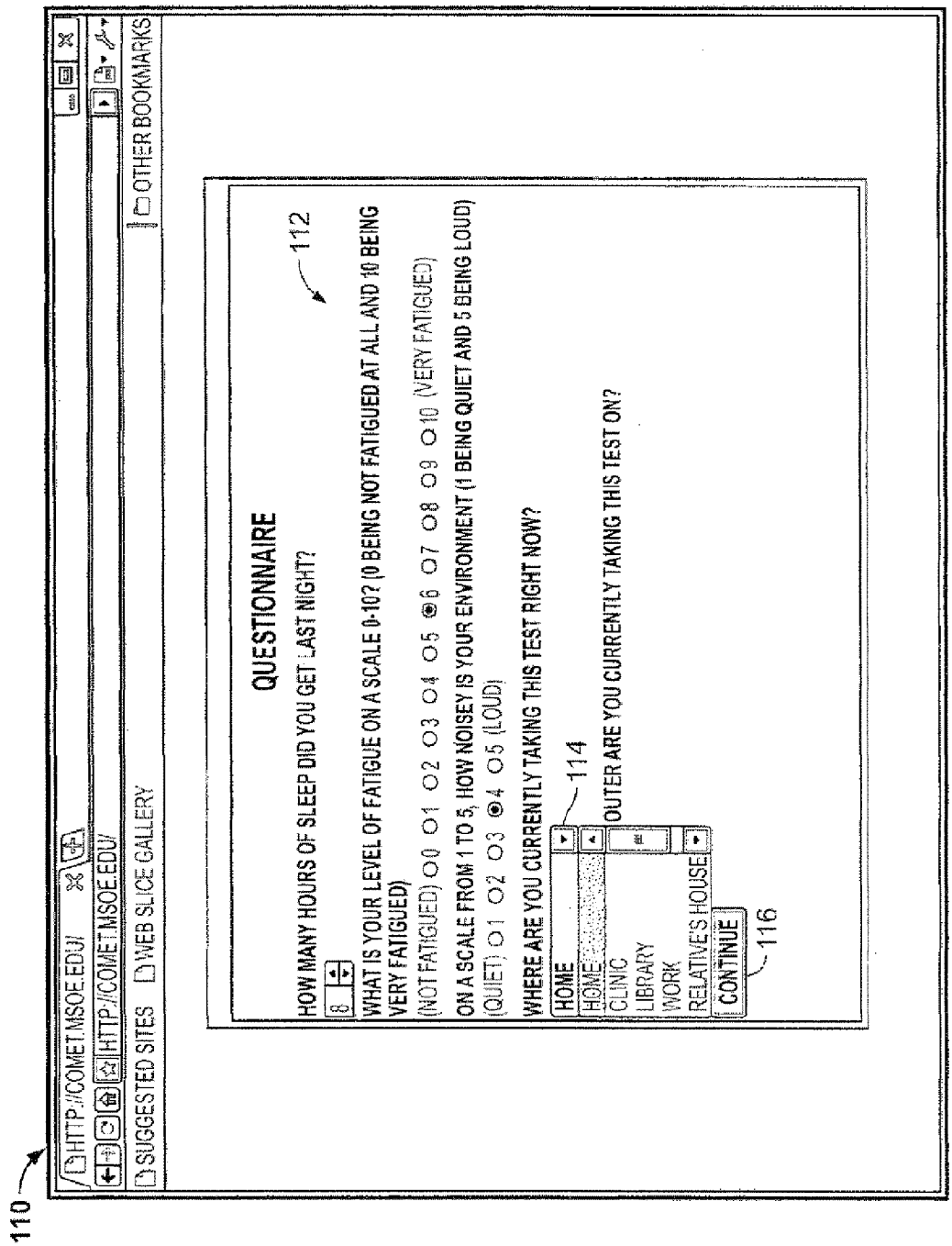
FIG. 4 depicts a patient's questionnaire that can be presented to a patient or clinician user, according to an example embodiment of the invention.

FIG. 4 depicts an example of a screen shot 110 including an example of a GUI element 112 for obtaining information pertaining to a user's general health condition, state of mind and environment in which the test is being taken. For example, the questions may include: "How many hours of sleep did you get last night?"; "What is your level of fatigue on a scale of 0-10?"; "On a scale from 1 to 5 how noisy is your environment?"; "Where are you currently taking the test right now?" Associated with this or other questions can be a drop down context menu 114 that can be utilized by the user to identify and select one of a predetermined number of responses. After answers to the question(s) have been entered, a user can hit a continue user interface element (a graphical button) 116 to continue.

Figure 5:
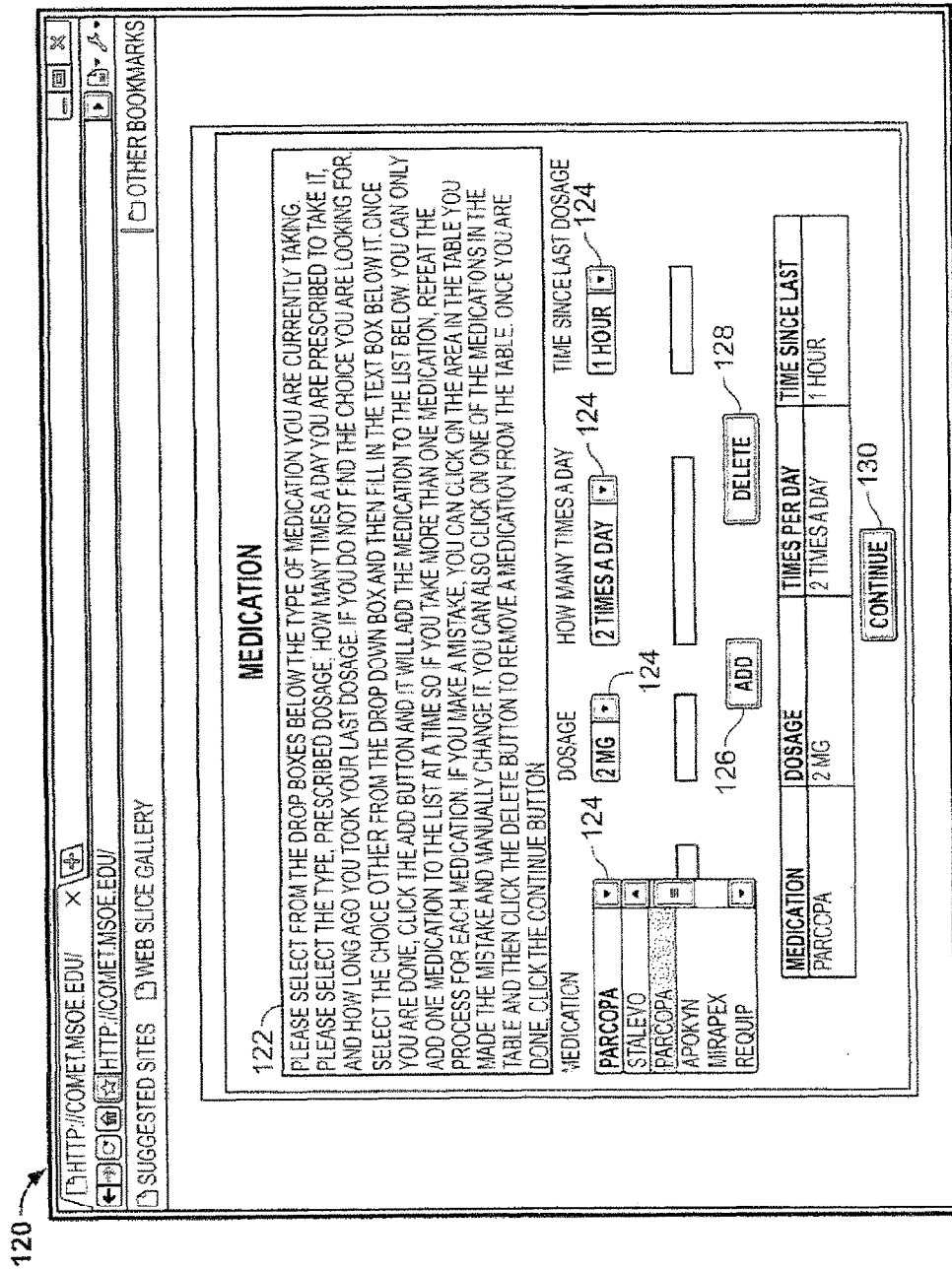
FIG. 5 depicts a screen shot for another part of a questionnaire that can be presented to a patient or clinician user, according to an example embodiment of the invention.

FIG. 5 depicts another screen shot example 120 that can be utilized to obtain information about medication that a given patient may be taking. The screen shot 120 includes a GUI element 122 having a variety of drop down context menus that can be utilized to identify medication(s), dosage, number of times per day the medication(s) is taken, and time(s) since last dosage of the medication(s). After the particulars associated with a given medication have been entered via the drop down context menus 124, a user may enter them into the system via an add user interface element 126. Similarly, an entry can be deleted or removed by selecting it with a cursor or other user interface element and in turn hitting a delete user interface element 128. After all medications have been appropriately entered into the medication form GUI element 122, a user can continue to the next phase of the testing process by hitting a user interface element or button 130. The medication information can be programmatically associated with test data to allow correlations to be determined, such as described herein. In an example embodiment, a clinician may enter some or all of the medication and/or other therapy information into the system.

Figure 6:
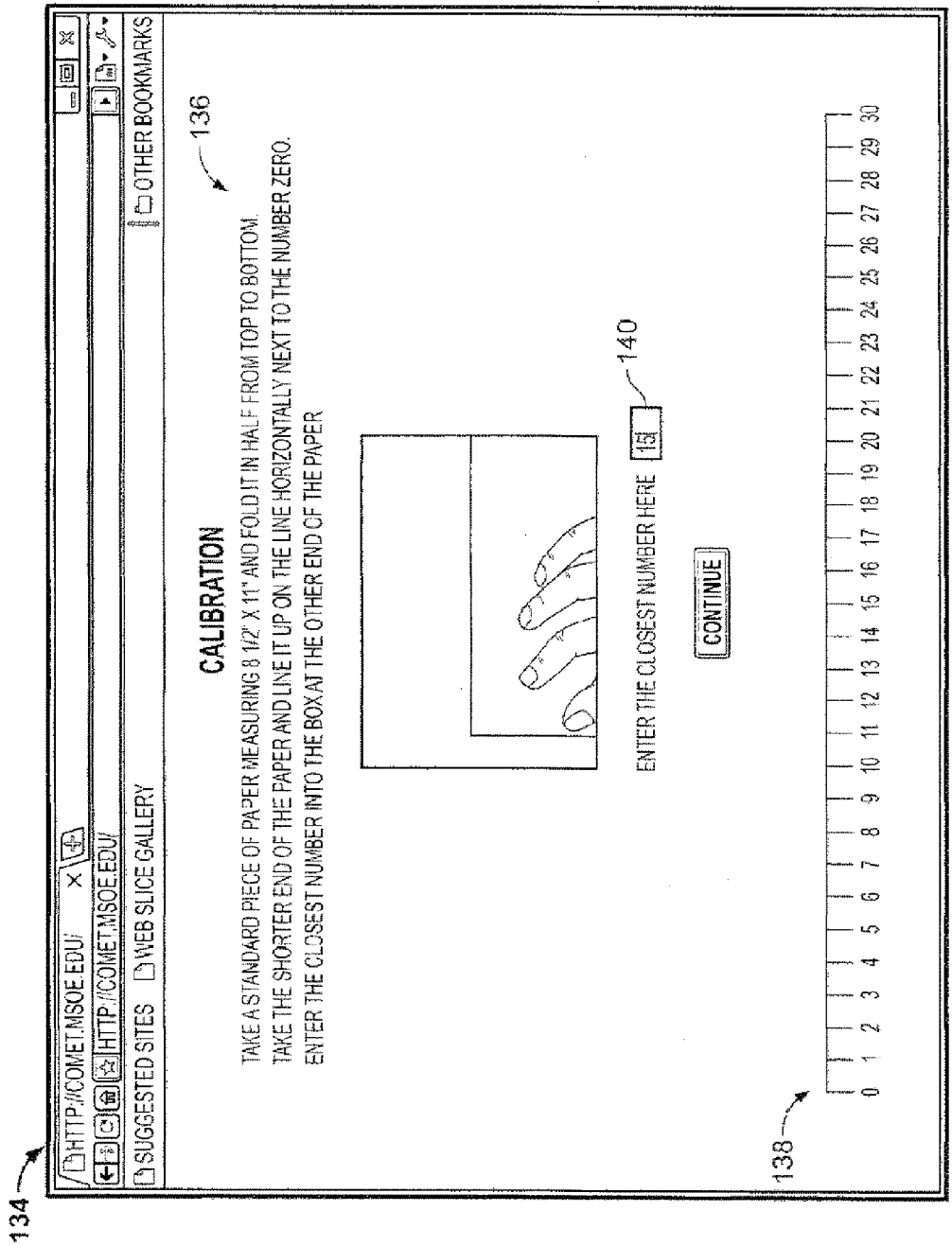
FIG. 6 depicts a graphical user interface (GUI) that can be utilized for calibration of a remote test device, according to an example embodiment of the invention.

FIG. 6 depicts an example of a screen shot 134 demonstrating a calibration GUI 136 that can be implemented for calibrating a remote user's computing device in a horizontal direction, according to an example embodiment of the invention. The calibration GUI 136 presents the user a scale 138 having a plurality of spaced apart markings or indicia, which are numbered consecutively in the example of FIG. 6 from zero to thirty. The calibration GUI 136 presents instructions to the user to fold a 8.5"×11" sheet of paper in half and place the shorter end of the folded sheet of paper adjacent the scale 138 with the one of the longer sides against the zero, and to enter the number closest to the other of the longer sides in a user entry dialogue box 140. The number entered into the dialogue box 140 relative to the actual size of the paper can be utilized to determine a size or dimensions of the display area presented on a user screen during the testing process. A similar calibration can be utilized in a vertical direction on a user screen such that both the horizontal and vertical dimensions can be known such that the results from the testing can be scaled appropriately.

Figure 7:
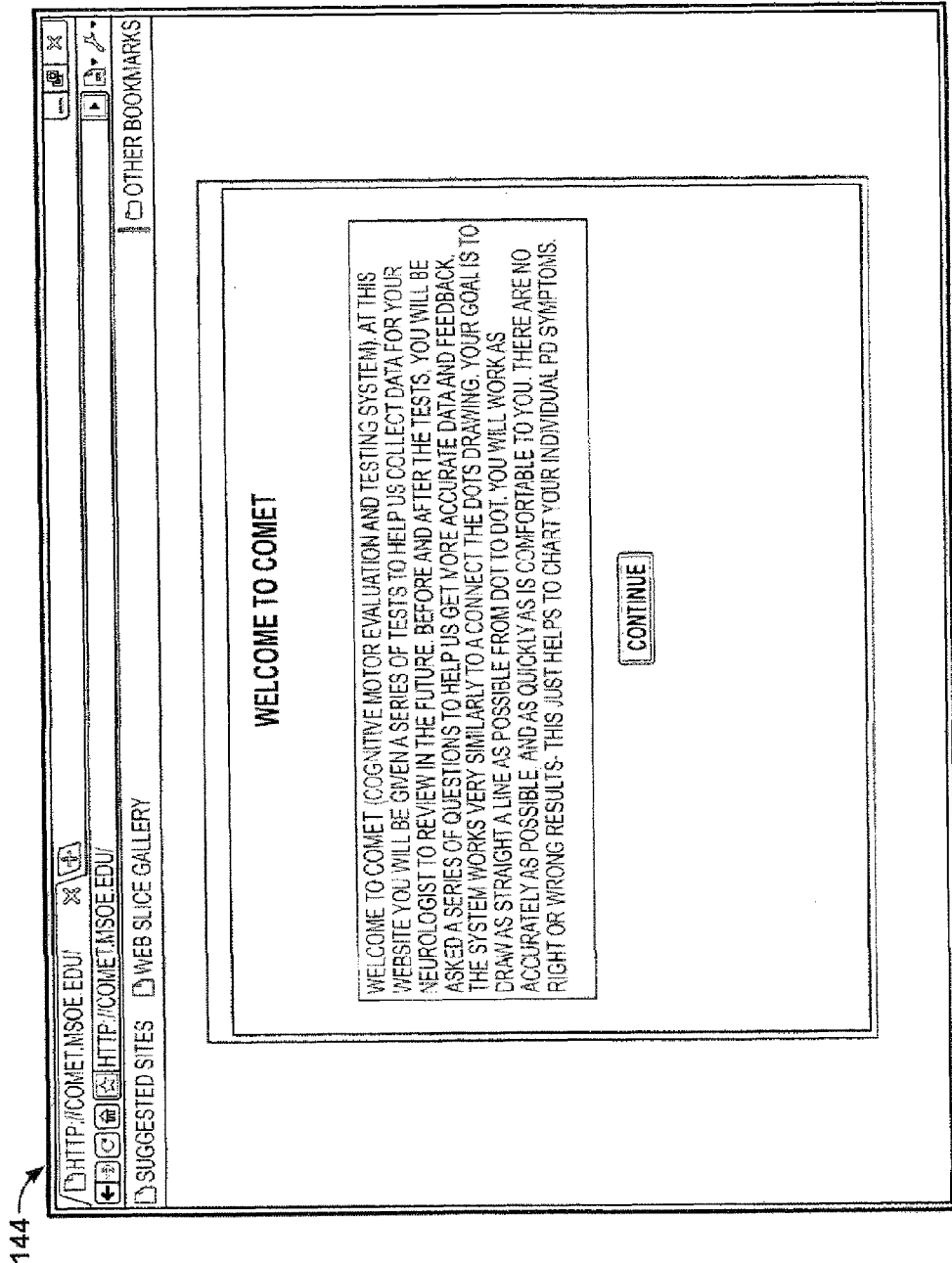
FIG. 7 depicts a screen shot GUI for an introductory screen that can be utilized for initiating a test, according to an example embodiment of the invention.

FIG. 7 depicts an example of a "welcome" screen shot that can be presented to the user to inform the individual that a test is about to begin and identify some additional information about the types of the test and how they will proceed. It should be understood that a few practice screens and tests can be implemented before beginning an actual test to familiarize a user with the testing process.

Figure 9:
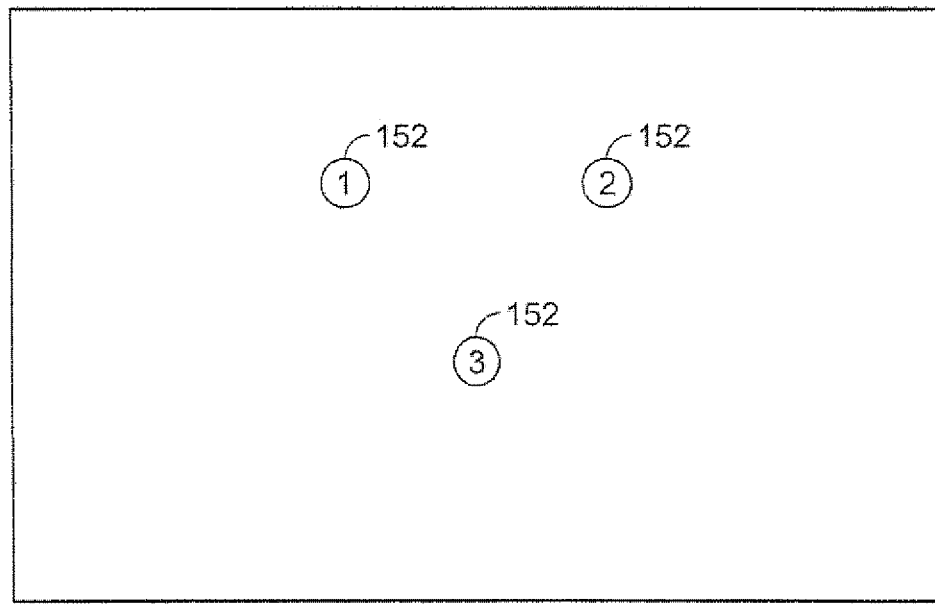
FIG. 9 depicts a "seven's test" GUI that can be implemented on a computer, according to an example embodiment of the invention.
Figure 10:
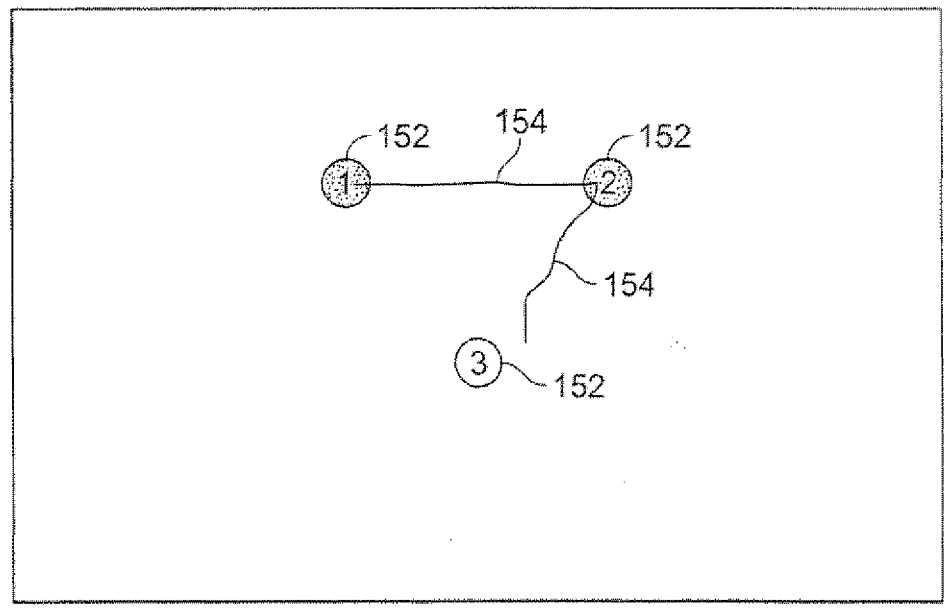
FIG. 10 depicts the "seven's test" GUI of FIG. 9 illustrating the test completed by a user, according to an example embodiment of the invention.

FIG. 8 depicts an example of an instruction GUI 146 that can be provided before performing a first test. FIGS. 9 and 10 depict an example of GUI 150 that includes a plurality of targets 152 for use in performing a "seven's test", for which a user is instructed to draw between targets a path having a shape similar to the number "7", for testing cognitive and/or motor skill. Each of the targets can be graphically constructed, as a graphical object that encompasses a region in the X/Y coordinates of a patient's graphical interface, such as in a screen. The GUI 150 corresponds to an example of a traditional "seven's test" in which a user is instructed to connect the dots using a pointing device such as a mouse, stylus, touch screen or the like. In the example of FIG. 9 three targets numbered numerically 1, 2, 3 are presented on the screen. A user is instructed to connect the targets 1 to 2 to 3 to draw a shape similar to the number "7". The system may record test data in association with performance of the test. The test data may include, for example, the position and temporal information of the path taken for connecting the targets. FIG. 10 shows an example of an outcome of a patient having connected target positions 1 and 2 but not target positions 2 and 3. To indicate the successful connection of target positions 1 and 2, the system has highlighted targets 1 and 2, in contrast to target 3 which is not highlighted. Referring back to FIG. 1, the test data acquired from FIG. 9 can include an identification of the position of each of the targets, a path taken by the patient for connecting or attempting to connect the targets, and/or temporal information associated with the path.

Thus, the information obtained with respect to the test outcome shown in FIG. 10 may include the coordinates of each of the targets 152 as well as the coordinates (or position) of the cursor or other pointing element during the test as the cursor or other pointing element moves between the respective targets and forms a corresponding line or path 154.

Figure 11:
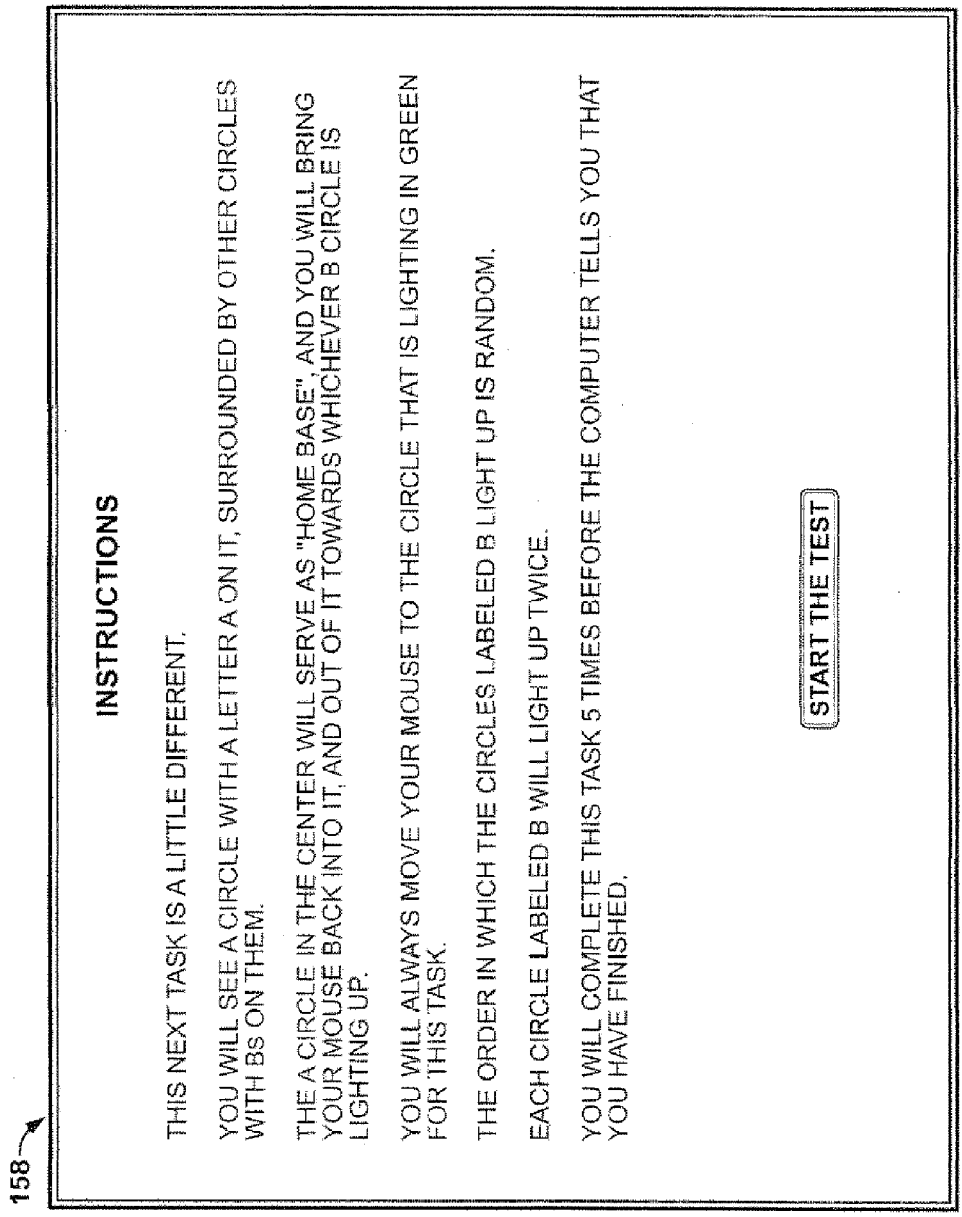
FIG. 11 depicts a screen shot GUI that can be utilized for providing instructions for a reaction test, according to an example embodiment of the invention.

FIG. 11 depicts an example of an instruction GUI 158 that can be provided before performance of a second test.

Figure 12:
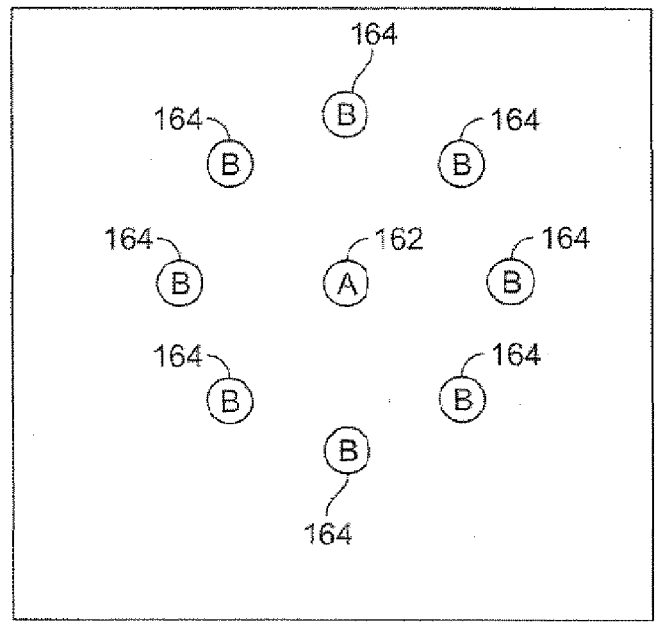
FIG. 12 depicts a reaction test GUI that can be implemented on a computer, according to an example embodiment of the invention.
Figure 13:
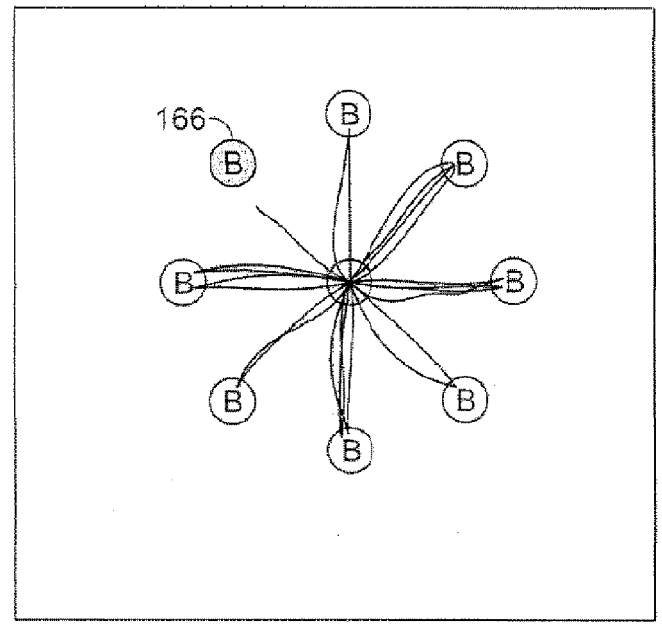
FIG. 13 depicts the reaction test GUI of FIG. 12 at least partially completed by a patient user, according to an example embodiment of the invention.

FIGS. 12 and 13 depict an example of a GUI 160 that can be provided in connection with performing a reaction time test with subsequent movement, such as a center-out test, for testing, e.g., cognitive ability. Thus, the GUI 160 includes a plurality of targets, including the center target 162 and a plurality of outer targets 164 in circumscribing relation relative to the center target. The center-out test can be performed to test reaction time of the user by displaying one of the outer targets 164 in a contrast color relative to the other targets 162 and 164 and in turn storing the time interval from displaying the contrasted target on the GUI 160 to the time the user begins to move a pointing device for connecting the central target 162 to the contrasted outer target 164. Additional information can be obtained during the process, including the position over time of the cursor relative to each of the respective graphical renderings of the targets, e.g., representing a path taken by the user between the center target 162 and the outer targets 164, and/or the corresponding times.

In FIG. 13, a partially completed center-out test is depicted showing one of the targets 166 having a contrast color relative to the other targets thereby designating the intended target for connection between the center target 162 and the contrast target 166. The center-out test can be performed such that different ones of the outer targets are selected in a predictable or random order one or more times.

Figure 15:
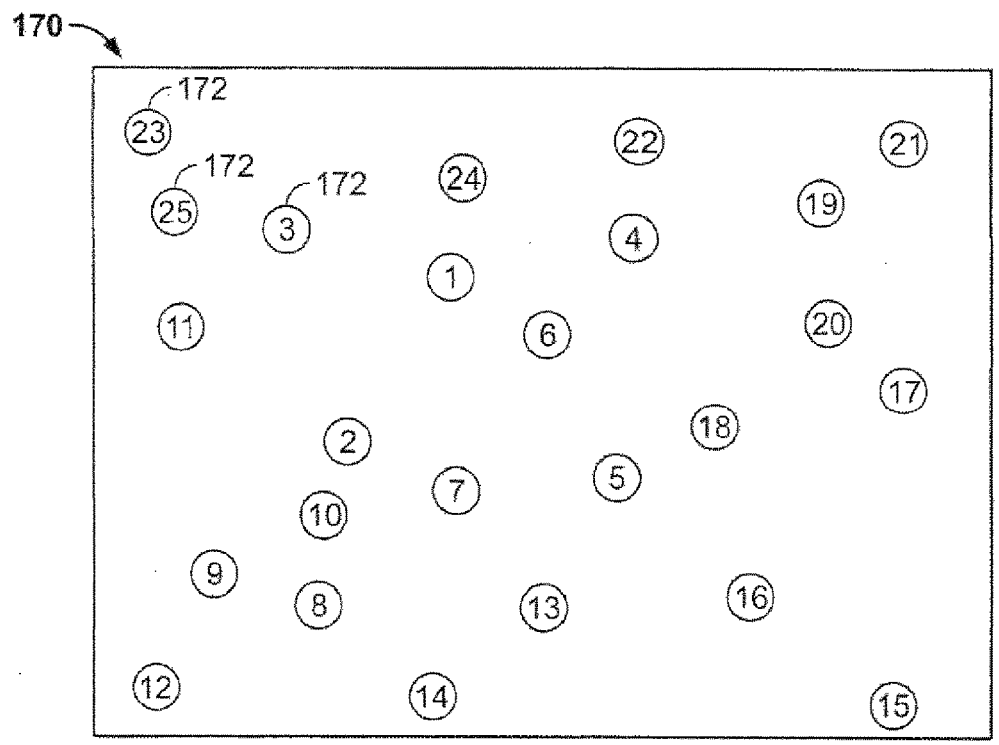
FIG. 15 depicts a trail making test (Part A) GUI that can be implemented on a computer, according to an example embodiment of the invention.
Figure 16:
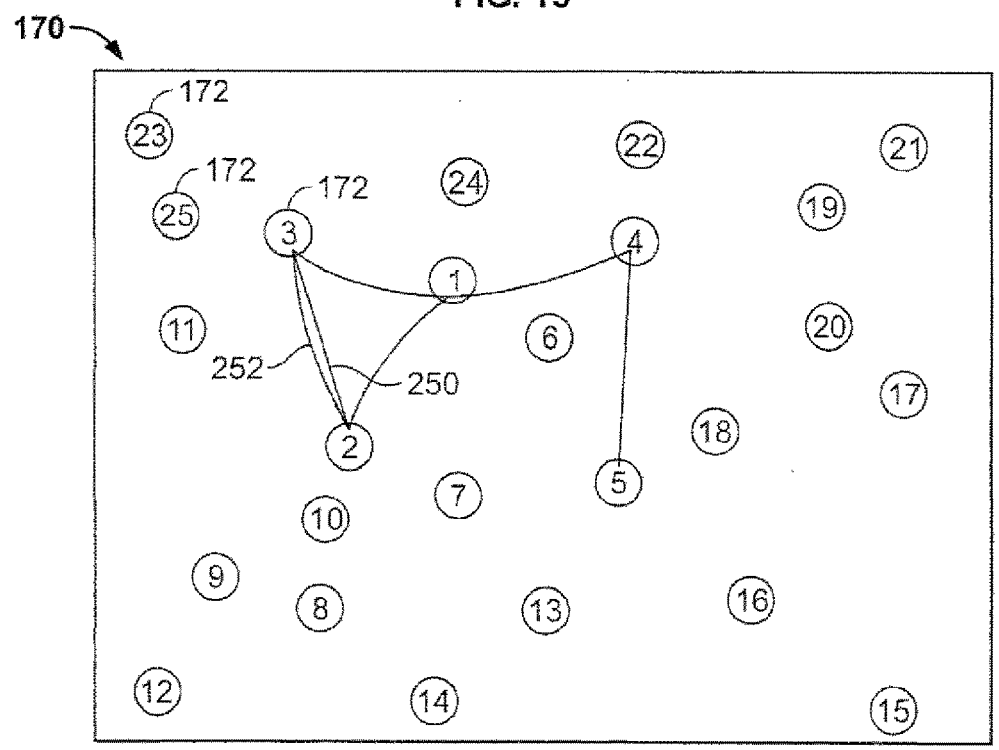
FIG. 16 depicts the trail making test (Part A) GUI of FIG. 15 partially completed by a patient user, according to an example embodiment of the invention.

FIG. 14 depicts an example of another instruction GUI 168 that can be presented to a user for providing instructions for performing a third test, including such as shown and described with respect to FIGS. 15 and 16.

FIGS. 15 and 16 depict an example of a test GUI 170 that can be utilized for performing a trail making test (Part A), for testing cognitive and/or motor skill. The trail making test (Part A) implemented via the GUI 170 may be used to assess both motor and cognitive information concurrently. For instance, a plurality of targets 172 are distributed across the display area provided by the GUI 170. In the example of FIGS. 15 and 16, the targets are numbered from 1 to 24 and the user (as instructed by the instruction GUI 168 of FIG. 14) is to connect the targets in a sequential order. The test engine can populate the display area for the GUI 170 in a pseudo random fashion such that each of the sequential targets can be interconnected by an ideal straight line without crossing a line interconnecting any other sequential targets. Thus, in addition to obtaining the position, velocity, speed and/or acceleration information, crossing lines can also be identified to provide a further indication of a patient's motor and cognitive function.

FIG. 16 depicts an example in which a patient has connected the first five targets with lines going from target 1 to target 2 to target 3 to target 4 and to target 5. Thus, from the example tests of FIGS. 15 and 16 information corresponding to the position of the cursor that is utilized to draw each line connected between sequentially numbered targets can be recorded and stored as test data in memory (e.g., local or associated with a server). In addition to the position data, temporal data can be obtained with each sample as well. Thus, the position and time data can then be provided as test data to the analysis system for evaluation, such as shown and described in further detail below.

Also depicted in FIG. 16 is a diagrammatic view of a line used in an analysis that can be performed to characterize a degree of error, e.g., by calculating an average error, a mean square error, or a root mean square error, for each of a plurality of respective lines interconnecting sequential targets 172 in the GUI 170. For example, referring to targets 2 and 3, this can be performed, for example, by comparing the relative positions of points along an ideal straight line 250 connected between targets 2 and 3 relative to a line segment 252 drawn by a patient (e.g., responsive to user-controlled movement with a pointing device) between the same respective targets. For instance, the same number of equally spaced sample points can be populated along the length of each line segment 250 and 252 and a corresponding means square error can be computed for differences between the sets of sample points. For example, the error values recorded for the sample points can be squared, then summed together, and then divided by the number of sample point pairs to provide the mean square error of the patient's line 252 relative to the ideal line segment 250. Those skilled in the art will understand and appreciate various types of estimators that can be utilized to compute a measure of how close the user's line 252 is to the fitted ideal (straight) line 250 between targets, such as including the sample mean, sample variance, analysis of variance, root mean square error, standard deviation as well as linear regression techniques.

For example, the resulting mean square error can further be utilized to compute a root means square error by taking the square-root of the mean square error for each of the line segments between targets. The root means square error thus can provide essentially an average measure of distance of the user's data points on the line 252 from corresponding points on the ideal line 250.

Figure 18:
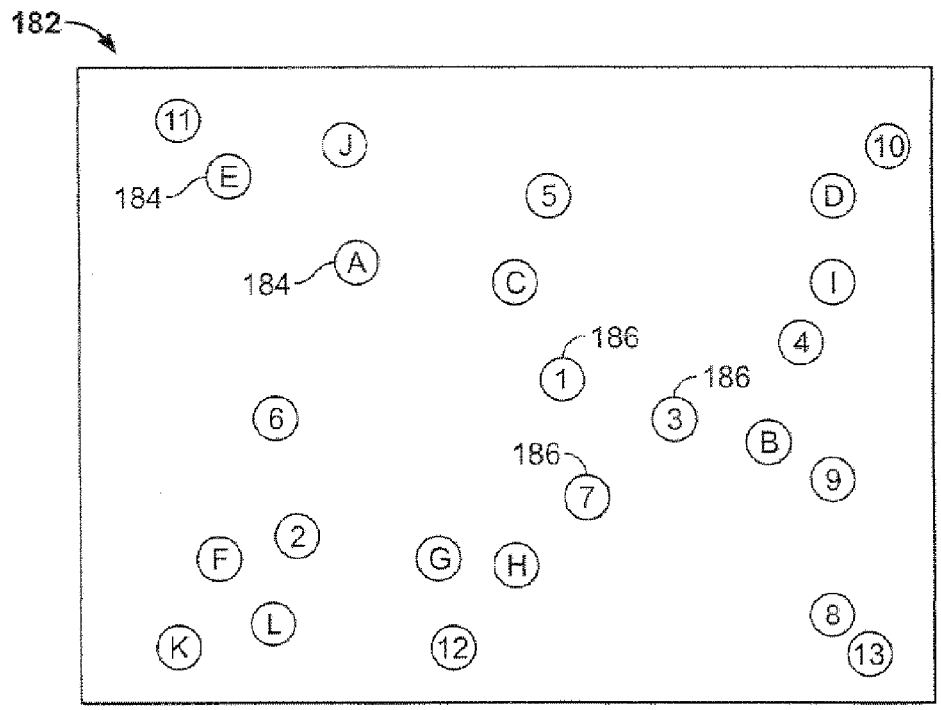
FIG. 18 depicts a trail making test (Part B) GUI that can be implemented on a computer, according to an example embodiment of the invention.
Figure 19:
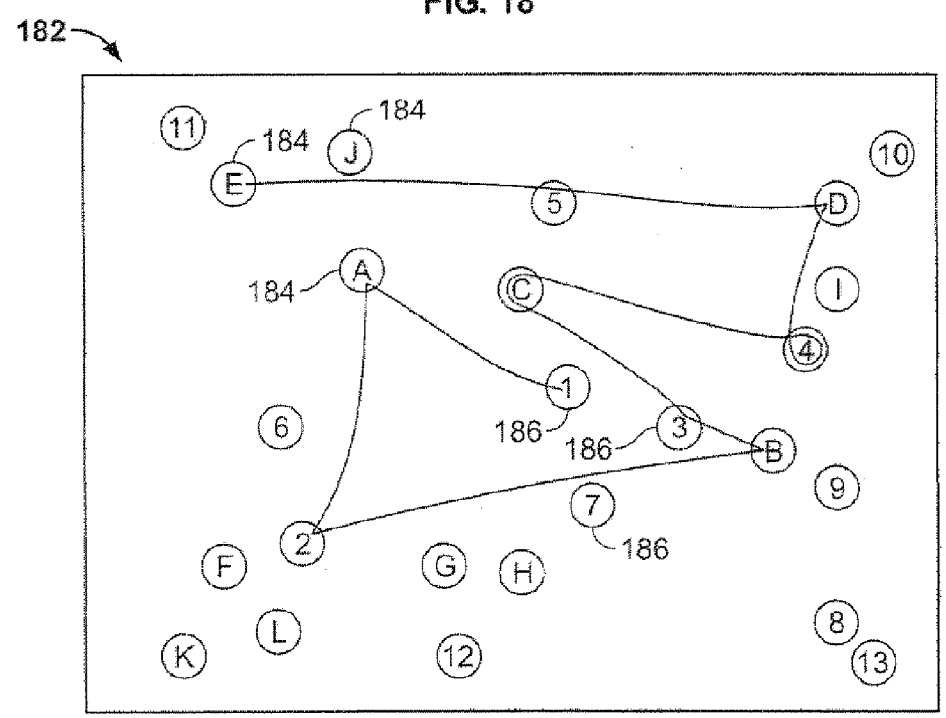
FIG. 19 depicts the trail making test (Part B) GUI from FIG. 18 partially completed by a patient user, according to an example embodiment of the invention.

FIG. 17 depicts an example of an instruction GUI 180 that can be provided for instructing a user for a trail making test (Part B) test such as shown in FIGS. 18 and 19, for testing cognitive and/or motor skill.

FIGS. 18 and 19 depict an example of a GUI 182 that can be presented to a user in connection with performing and recording information associated with a trail making test (Part B). The GUI 182 presents a plurality of targets positioned in a display area according to application data determined by a corresponding test application. In the examples of FIGS. 18 and 19, the targets are circles, each of which defines a bounded region having a corresponding set of coordinates. In the display GUI 182, a portion of the targets, indicated at 184, have letters ranging consecutively from A through H and another corresponding portion of the targets, indicated at 186, have numbers ranging consecutively from 1 through 13. Those skilled in the art will understand that the test engine can be programmed to automatically generate any arrangement of targets consistent with the format of the trail making test (Part B), which arrangement may be part of the test data provided to the analysis engine 16.

The trail making test (Part B) implemented by GUI 182 may be used to assess both motor and cognitive information concurrently. For instance, the instructions (e.g., via the instruction GUI 180 of FIG. 17) specify that a user-patient is to alternate between consecutive sequential letters and numbers by connecting respective targets with straight lines, similar to what is shown in FIG. 19 up to letter E, beginning with the lowest number to the lowest letter, to the second lowest number, to the second highest letter, etc. Thus, FIG. 19 shows an example outcome of a test in which a user has used a cursor having a position that can be tracked via the corresponding API. The system is configured to dynamically render a graphical depiction of a line onto the display GUI 182 in response to movements of the cursor, for example, via a corresponding pointing element, such as a mouse, stylus or touch screen. Information associated with the position and times associated with the positions, representing times for each of the movements, can be recorded for subsequent analysis and evaluation as described herein.

Figure 20:
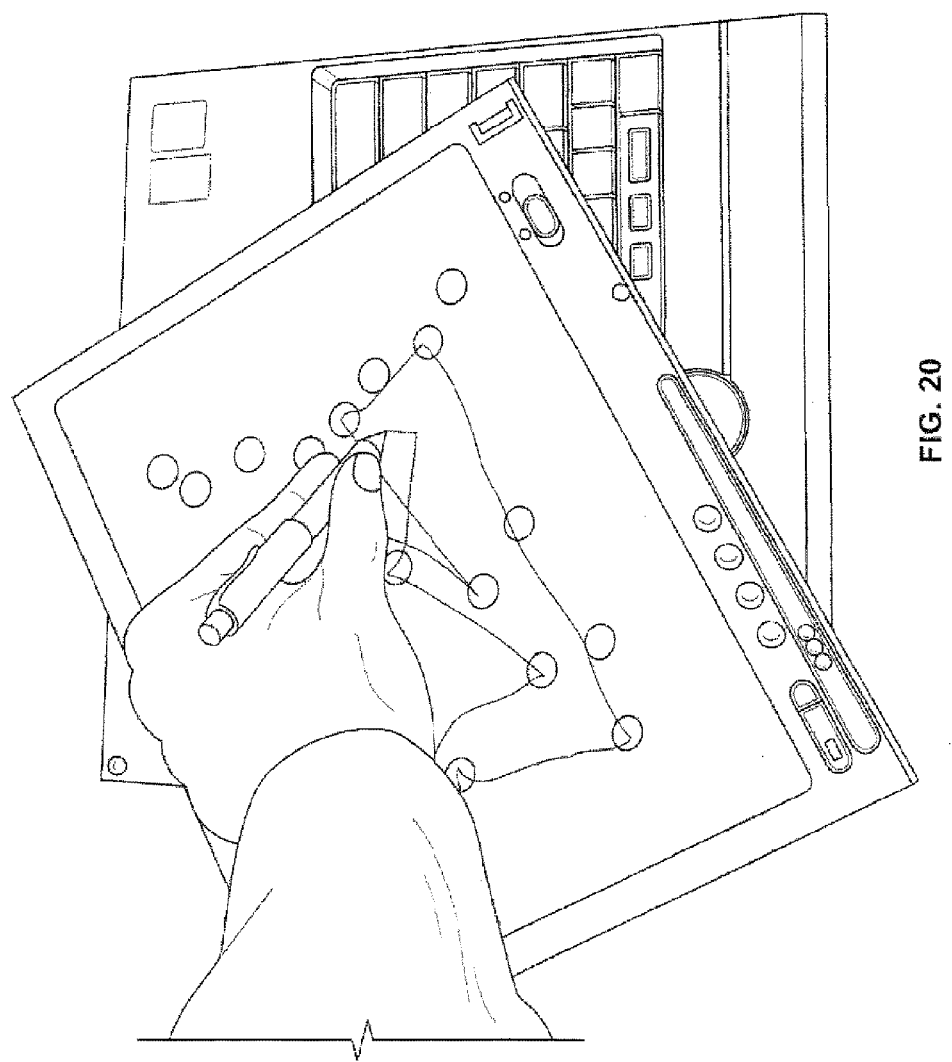
FIG. 20 depicts a trail making test being performed on a surface of a tablet personal computer (PC) by a patient user, according to an example embodiment of the invention.

FIG. 20 depicts an example embodiment in which the user computing device for performing a test is implemented as a tablet personal computer (PC). Thus, in this example a user holds a stylus (similar to a pen) on a corresponding touch screen for drawing interconnecting lines between targets, such as is shown in FIG. 18. It is understood that a user could use the user's fingers to draw the interconnecting lines.

Figure 21:
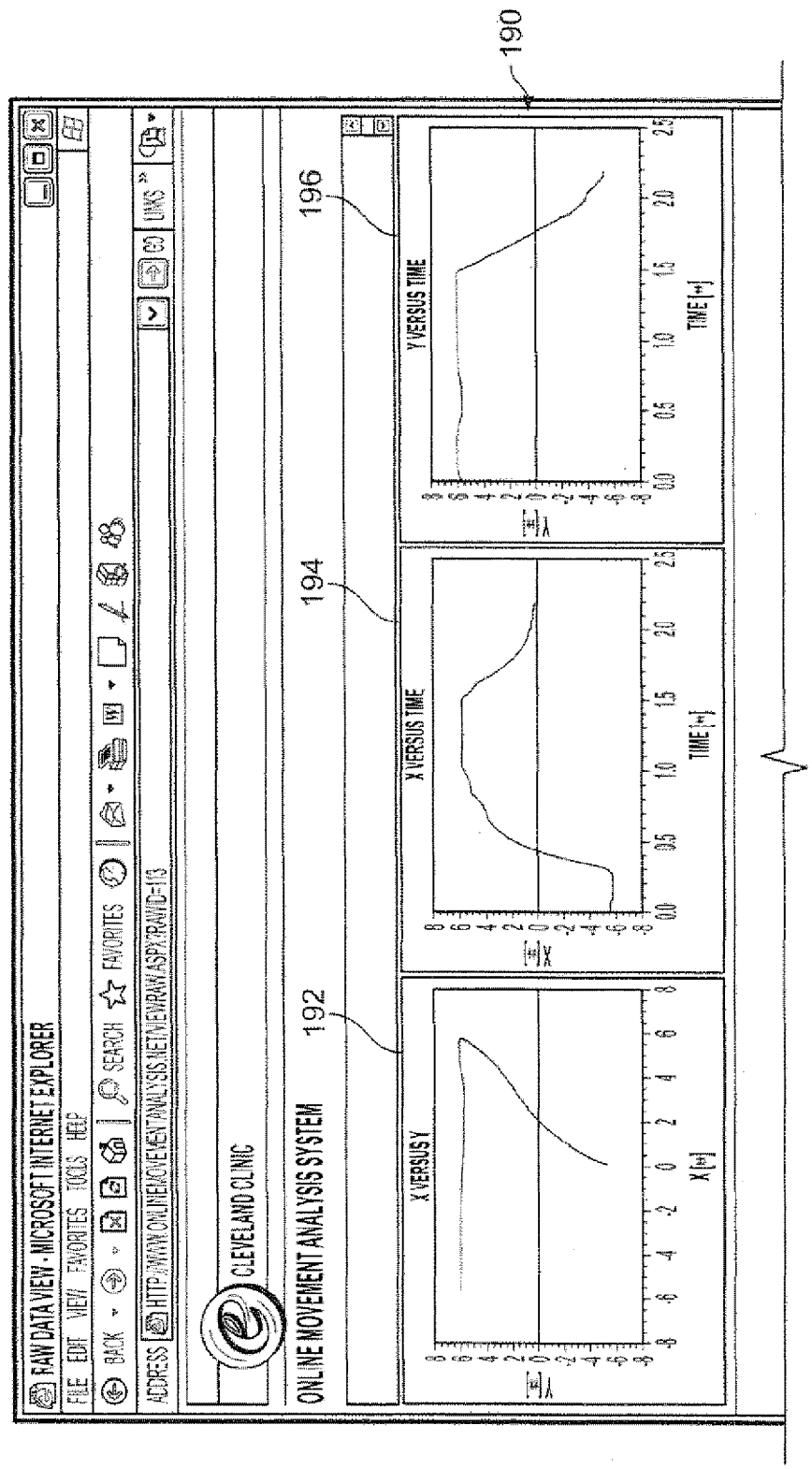
FIG. 21 depicts test results that can be displayed to a user via a management user interface, according to an example embodiment of the invention.
Figure 21:
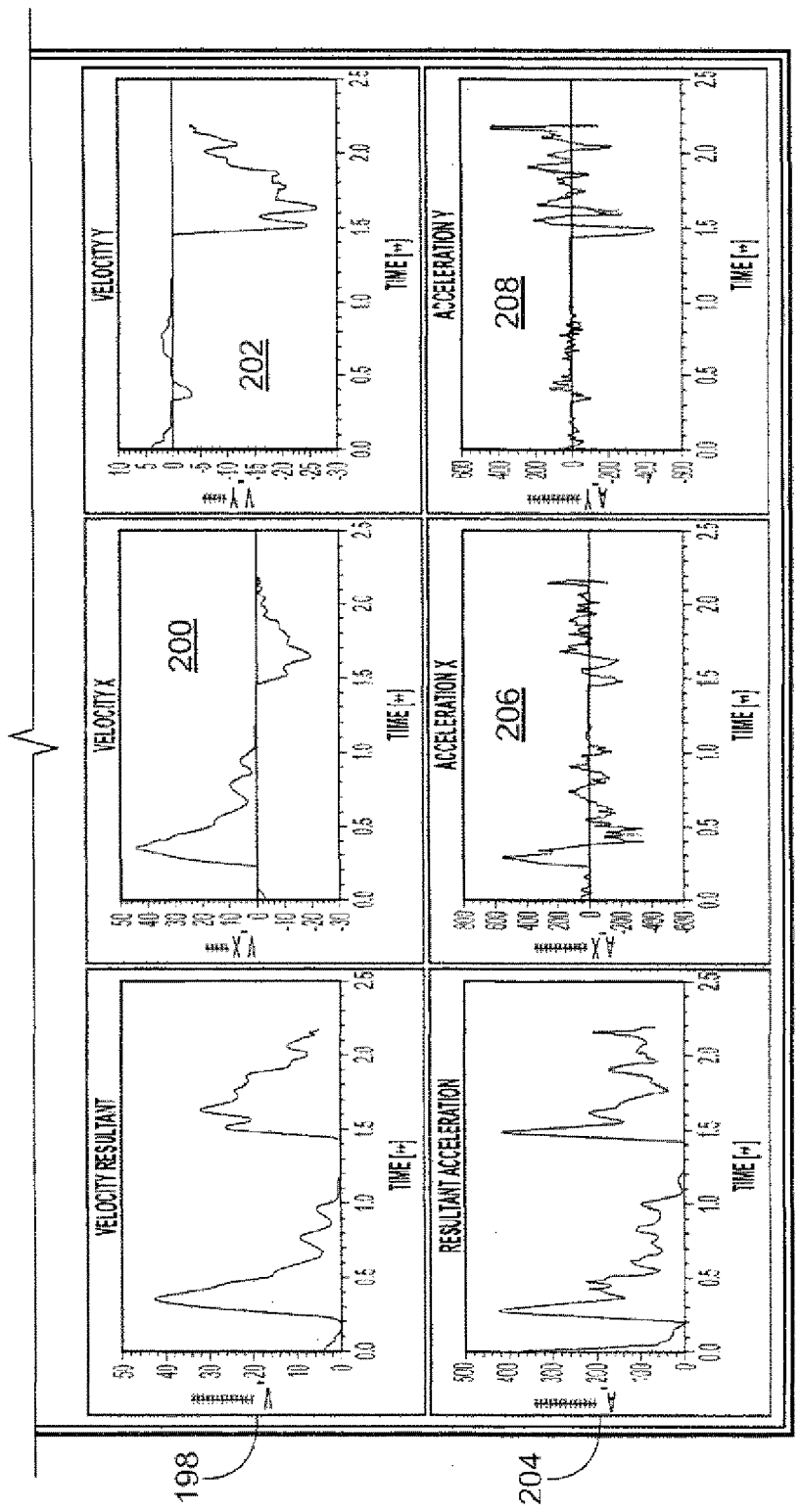

FIG. 21 depicts an example of analysis data that can be generated and displayed in a GUI 190 as a function of test data acquired from a respective test. The resulting analysis data can be presented in a variety of formats, which may be selected by a user. In the GUI 190, a plurality of different plots are shown for depicting different information that can be computed based upon the acquired position and respective time data for a given test. Each of the plots in the top row indicates position information, the middle row of plots indicates velocity information and the bottom row indicates acceleration information for a given test. The position data can be correlated into corresponding velocity and acceleration information by analysis of change over time of the X and Y coordinates of the cursor obtained from the samples recorded during a test. In the example of FIG. 21, the GUI depicts analysis data for a "seven's test" such as shown and described with respect to FIGS. 9 and 10. The GUI 190 can be presented via a management user interface 66 or researcher user interface 72 for analysis and evaluation by an authorized user.

By way of example, the plot 192 depicts X position versus Y position, thereby showing the graphical object as a pair of interconnected line segments in a relative coordinate system based upon user input with a corresponding pointing device, representing the path the user took between the targets of the "seven's test." A representative plot 194 shows the X data of plot 192 plotted as a function of time, and plot 196 shows the Y data of plot 192 plotted as a function of time.

A plot 198 depicts the velocity information corresponding to the changes in the X,Y positions plotted in plot 192 over the time period in which the changes occurred, i.e., during the test. Plot 200 depicts velocity in the X direction with respect to time such as by taking the change between plotted positional points in plot 194 over the plotted time in which such change occurred. Similarly, plot 202 depicts velocity of the Y direction with respect to time such as by taking the change between plotted positional points in plot 196 over the plotted time in which such change occurred.

Figure 23:
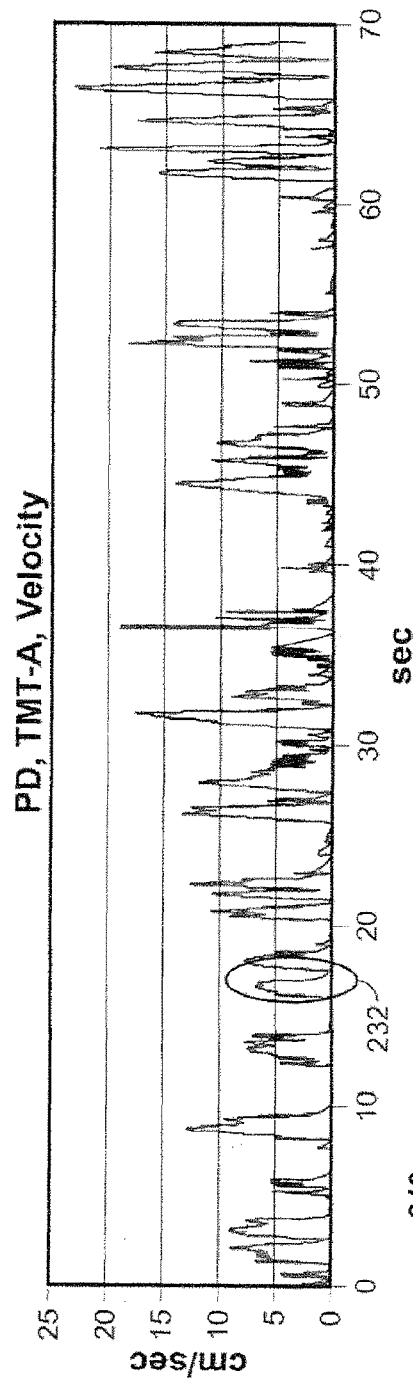
FIG. 23 depicts velocity data that can be computed for a trail making test (Part A), according to an example embodiment of the invention.
Figure 24:
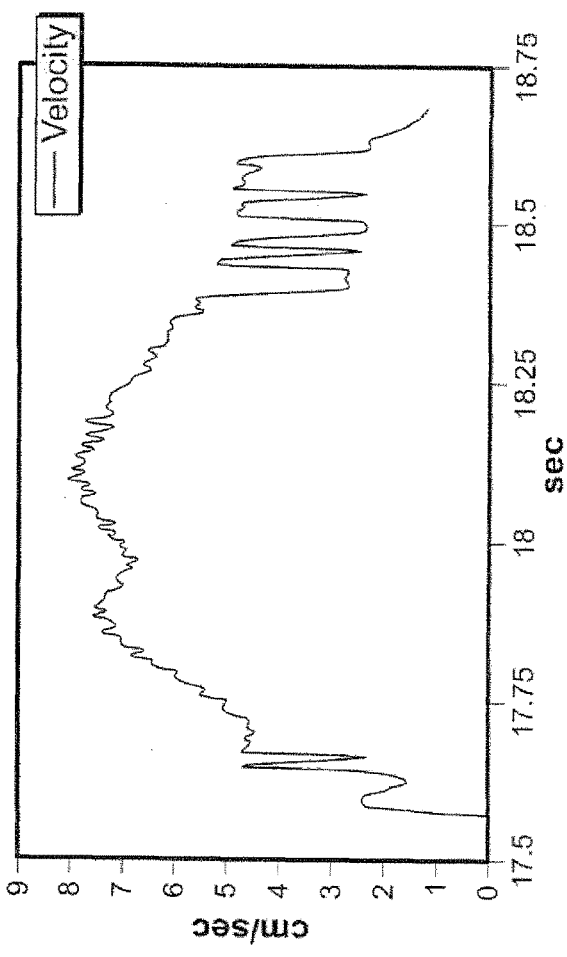
FIG. 24 depicts an enlarged view of a portion of the test from FIG. 23 that can be generated based upon data acquired from a patient user, according to an example embodiment of the invention.

Similarly, FIG. 23 depicts a plot 230 of velocity as a function of time (cm/sec) that can be obtained from data acquired from a trail making test (Part A) implemented according to an aspect of the invention. An enlarged view of a portion 232 of the waveform formed by the plot 230 is depicted in FIG. 24 at 240.

Referring again to FIG. 21, another set of plots 204, 206 and 208 depict the acceleration for each of the respective curves. For instance, the plot 204 displays a plot of acceleration versus time, such as by taking the change in velocity values of plot 198 over the corresponding time period in which such change occurred. The plot 206 corresponds to the acceleration in the X direction versus time such as by taking the change in velocity values of plot 200 over the corresponding time period in which such change occurred. Similarly, the plot 208 displays a plot of acceleration in the Y direction versus time, such as by taking the change in velocity values of plot 202 over the corresponding time period in which such change occurred.

The separate data concerning the movement in the X and Y directions, respectively, e.g., one or more of plots 194, 196, 200, 202, 206, and 208, may be used, for example, to characterize skill with respect to different directions.

As noted above, the index calculator 40 may calculate a score characterizing a test taker's performance on one or more administered tests. In an example embodiment of the invention, the analysis engine 16 may compare an overall curve shape of one or more of the types of graphs shown in FIG. 21, e.g., which plot velocity and/or acceleration, to stored graph shapes. For example, the shape of a plotted velocity or acceleration may be compared to a stored smooth bell-shaped curve, which may be considered to represent ideal motion by a healthy person when taking a test. The analysis engine 16 may score the graphs of the test taker's motion, such that the closer the shapes of the graphs to the stored graph shapes, the higher the score. Similarly, the analysis engine 16 may determine the extent (with respect to number and/or degree) to which the graph(s) include spikes, where such spikes may be used as indications of low quality movement including significant and/or many corrective and/or tremor-like motions.

The graph shape score(s) may be used, for example, by the index calculator 40, to calculate the index, which may be stored and output, for example, via the management user interface 66. It is noted that the index may be based on a number of factors. In an example embodiment, different factors, e.g., including the graph shape score, may be multiplied by respective weighting values, for example, depending on ranked significance with respect to the overall index.

Figure 22:
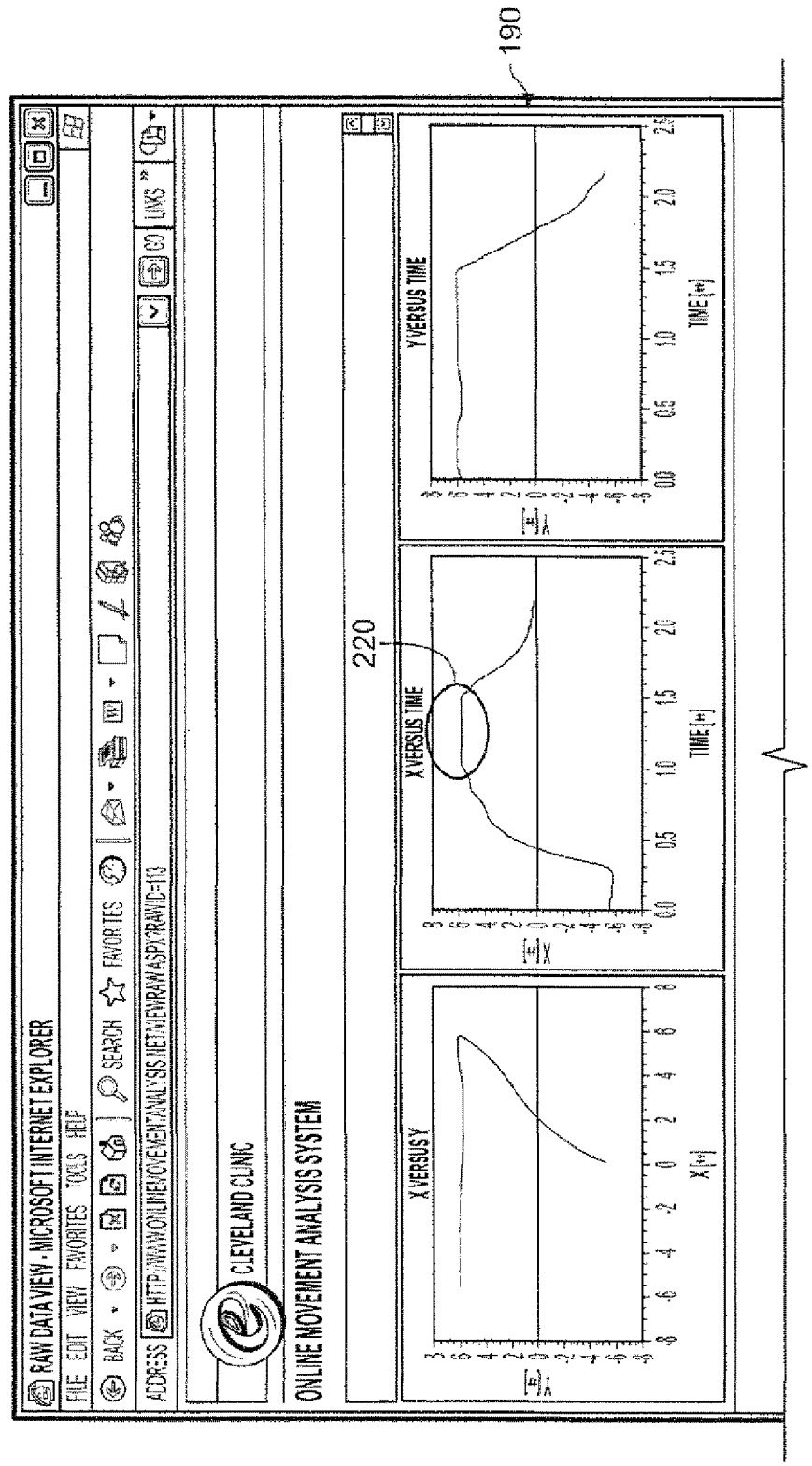
FIG. 22 depicts the management user interface of FIG. 21 demonstrating an example of where data can be obtained for use in assessing neurocognitive functions of a patient user, according to an example embodiment of the invention.
Figure 22:
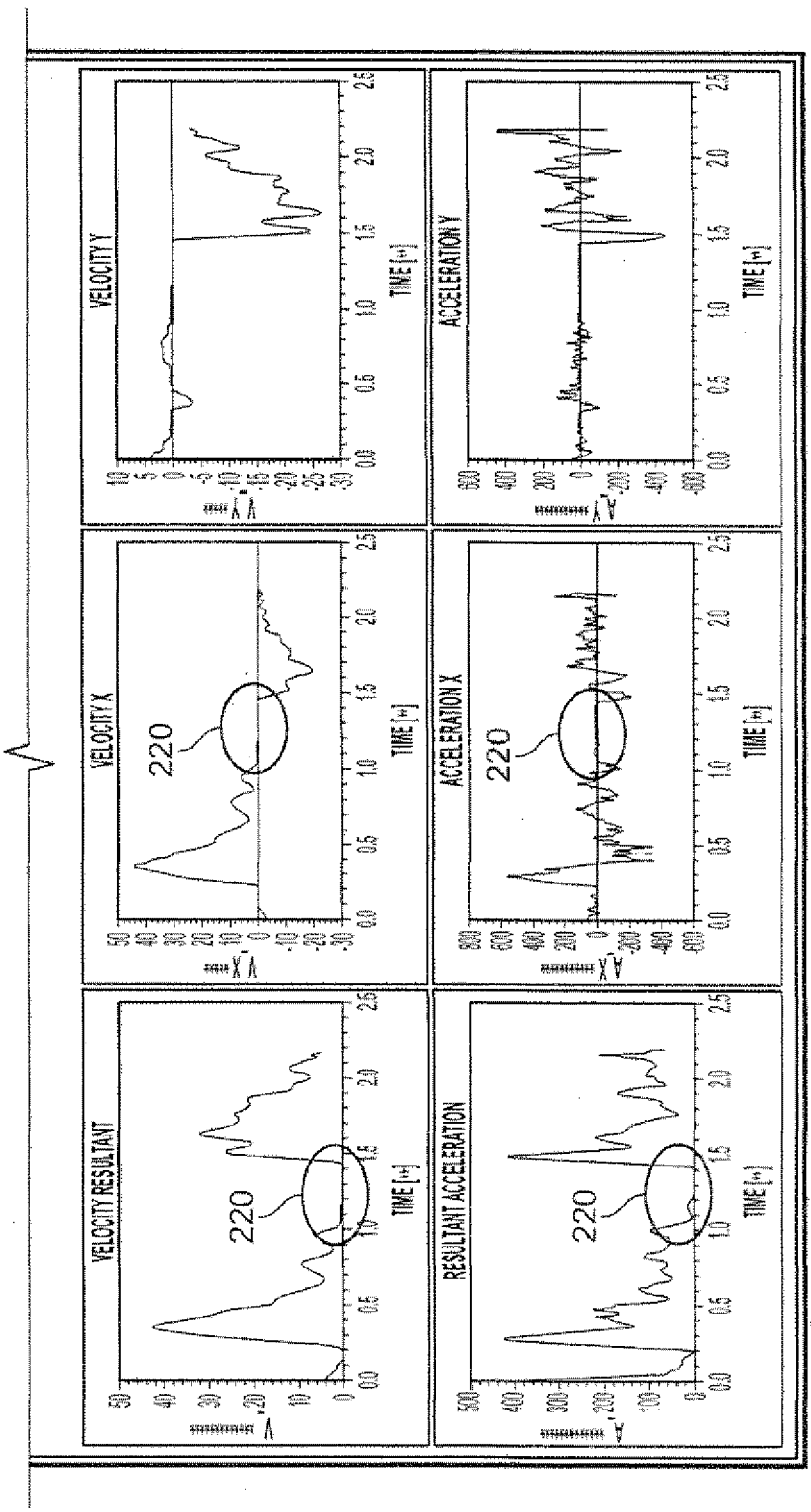

By way of further example, FIG. 22 is a reproduction of the GUI 190 shown in FIG. 21 in which selected portions of position and kinematic data have been identified by circles 220 corresponding to relevant data that can be utilized by the cognitive calculator 38 for computing dwell time. For example, dwell time can correspond to an amount of time that a cursor or other user-controlled graphical interface element resides within a bounded region, such as a defined border of a target. Such bounded regions can be identified in the testing data according to position data (e.g., X and Y coordinates) for each of the targets populating a test GUI. The identified regions for which dwell time is calculated can be identified by identifying the X and Y positions corresponding to each time during which no change occurs in the X and Y position or a period in which there is no velocity (e.g., from plot 198).

Figure 25:
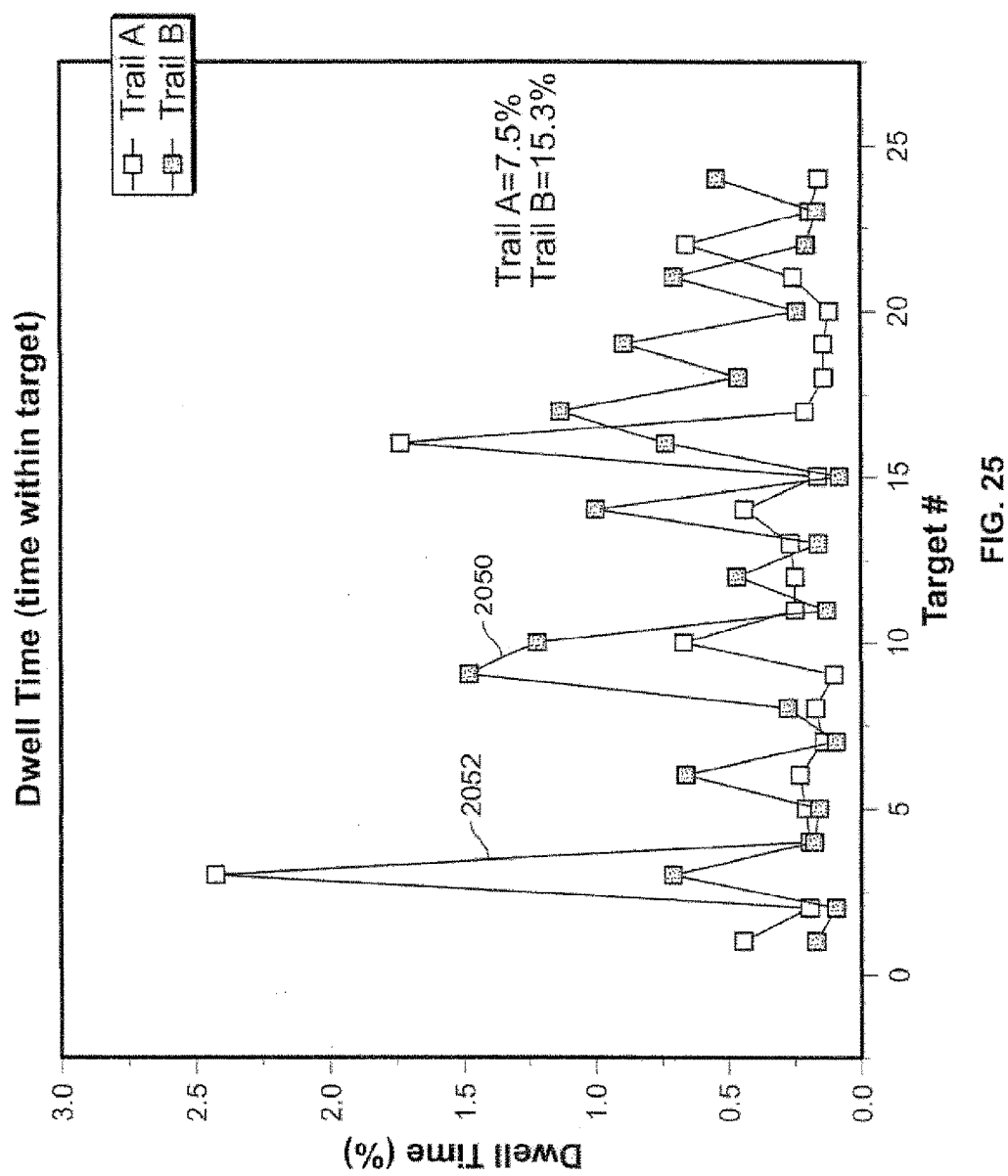
FIG. 25 depicts dwell time data computed for a plurality of targets for a trailing making test (Part A) and a trail making test (Part B) test, according to an example embodiment of the invention.

FIG. 25 depicts example plots 2050 and 2052 of dwell time that can be computed for a trail making test (Part A) and a trail making test (Part B), respectively. The abscissa corresponds to target number displayed in the trail making tests, and the ordinate corresponds to the percentage of the overall time of the duration of the administered tests in which the cursor dwelled in the corresponding target. As described above, the dwell time corresponds to a time during which a cursor/pointing object is within a given pre-defined X-Y position range that encompasses a displayed target. Thus, the dwell time can be determined by correlation of position information (e.g., indicating that the cursor is within a bounded target) and velocity information (e.g., indicating that the cursor is either not moving or is moving within the bounded target at a rate that is below a predetermined threshold). It will be appreciated that motor function information can also be acquired concurrently with cognitive data represented by dwell time by computing and analyzing corresponding kinetic information. For example, in PD patients, tremor predominantly occurs when the patient is in a resting condition. That is, when the patient's hand, for example, is purposefully moving, there is little, if any, tremor, while, when the patient's hand is not purposefully moving and is in an essentially resting position, there may be significant tremor, e.g., at a substantially constant 3-8 Hz frequency. Accordingly, the dwell time information may be used as an indicator of which data is significant for measuring tremor in PD patients. For example, the system may determine a measure for tremor from data corresponding to where there was a determined dwell period, in which the user's hand was essentially in a resting position. This concurrent kinetic information can be employed to assess motor function (e.g., the patient could have some small movements during this time, especially if they have tremor) while cognitive function (e.g., pertaining to information processing and set switching) during this time is also analyzed.

In an example embodiment of the invention, the system and method may be used to administer and obtain data for certain tests used to measure only motor function, e.g., related to finger tapping or tapping between two points. In an example embodiment of the invention, the system and method may be used to administer and obtain data for certain tests used to measure only cognitive function, e.g., the Mini Mental State Exam or Raven's Progressive Matrices tests.

FIG. 26 depicts an example of a management GUI 260 that can be utilized to provide access to test data by a user having an appropriate level of authorization. Each set of test data can be associated with a patient via name or other identifying information. As shown in the GUI 260, there can be any number of raw data elements for a given patient, which may generally depend on the test or tests that have been conducted. Each set of raw data, for example, can correspond to a separate set of test data for a given one of the tests or phases (or repetition) of a given test.

FIG. 27 depicts a GUI 270 that can be utilized for managing protocols such as through a management user interface 66 implemented in a system. The protocols management GUI 270 can be utilized, for example, for identifying testing protocols being utilized for a given patient test process. In the example of FIG. 27, the GUI includes selection interface elements 272 that can be utilized to identify protocols set for a patient, such as indicating whether a deep brain stimulator was on or off during the respective tests or the medications and/or dosage thereof administered to the patient at the time of the respective tests. A user, such as a clinician, thus can select a set of protocols associated with a given patient to help understand the effect a given condition has relative to the set of test data acquired for each patient during a given test session.

For instance, these protocols can be implemented and corresponding sets of test data evaluated to ascertain the effects on various conditions such as whether a DBS is on during the test or off as well as whether a patient is on their medication at a prescribed dose or not, and the effect of such a condition on the performance of a test. Those skilled in the art will understand various other protocols and combinations of protocols that can be utilized for specifying patient control parameters associated with a given set of tests.

In view of the foregoing, it will be appreciated that systems and methods have been described that can be implemented to provide a battery of cognitive and motor tests to remotely assess neurological disorders such as neurocognitive and neuromotor disorders such as, for example, PD, Alzheimer's disease, multiple sclerosis, dementia, amyotrophic lateral sclerosis (ALS), Parkinsonian syndrome, trauma-induced brain injury, stroke and multiple systems atrophy (MSA). The systems and methods enable the testing to be performed remotely by a patient-user, and the collection of data in a central data repository, such as to provide access to such information by a clinician and to facilitate further research.

In view of the foregoing structural and functional description, those skilled in the art will appreciate that portions of the invention may be embodied as a method, data processing system, or computer program product. Accordingly, these portions of the invention may take the form of an entirely hardware embodiment, an entirely software embodiment, or an embodiment combining software and hardware, such as shown and described with respect to the computer system of FIGS. 1 and 2. Furthermore, portions of the invention may be a computer program product including a hardware computer-readable storage medium having computer readable program code on the medium. Any suitable computer-readable storage medium may be utilized including, but not limited to, static and dynamic storage devices, hard disks, optical storage devices, and magnetic storage devices.

Certain embodiments of the invention have been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, when executed by the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 28:
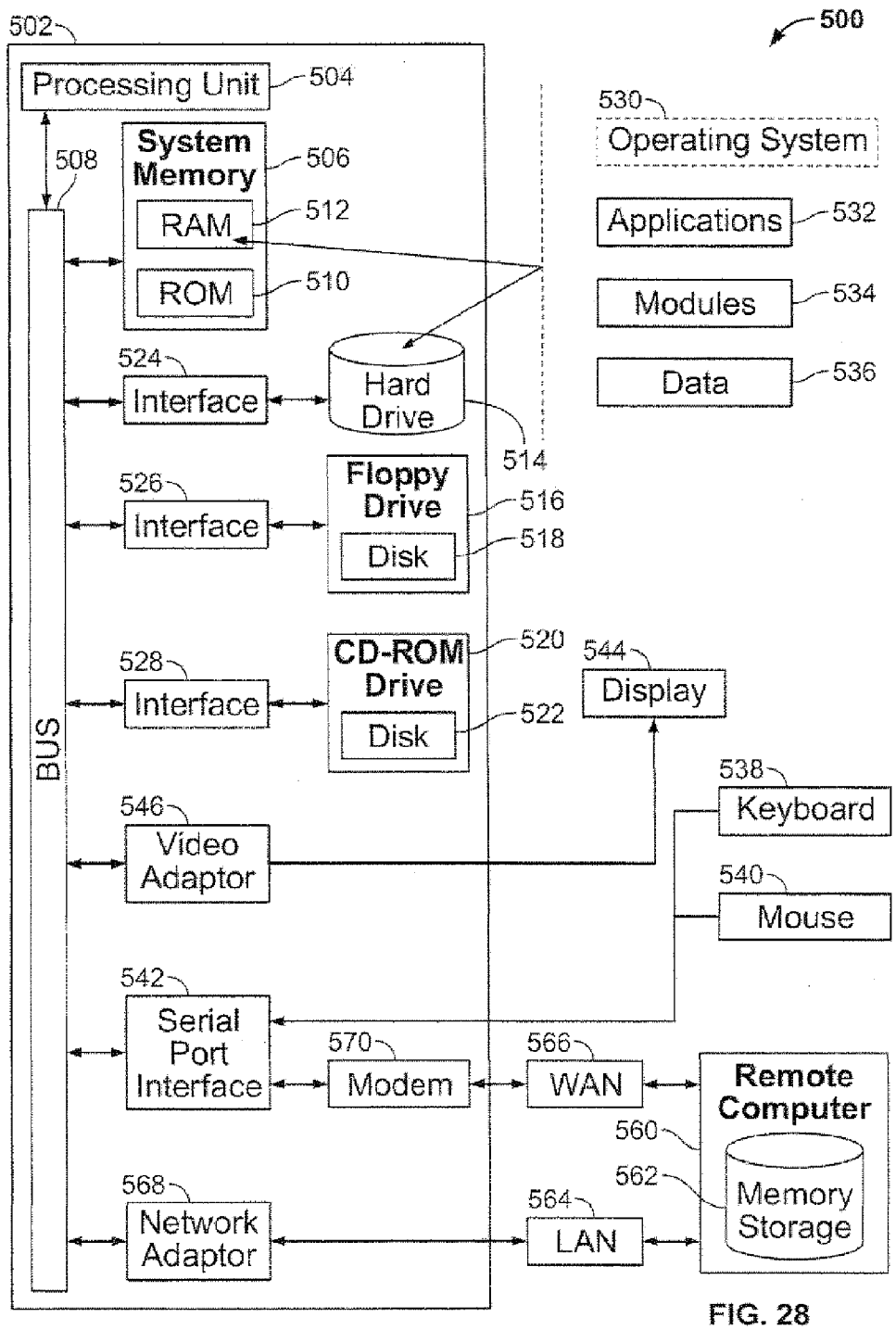
FIG. 28 depicts a computing environment that can be utilized for implementing systems and methods described herein, according to an example embodiment of the invention.

In this regard, FIG. 28 illustrates one example of a computer system 500 of the type that can be utilized to implement one or more embodiments of the systems and methods described herein for testing and analyzing motor and cognitive function of a patient. The computer system 500 can be implemented on one or more general purpose networked computer systems, embedded computer systems, routers, switches, server devices, client devices, various intermediate devices/nodes and/or stand alone computer systems. Additionally, the computer system 500 or portions thereof can be implemented on various mobile or portable clients such as, for example, a laptop or notebook computer, a personal digital assistant (PDA), tablet computer, smartphone (see, e.g., FIGS. 33-34) and the like.

The system 500 may include a computer 502, which may function, for example, as any of the user devices 54, 56, and 58 and/or the server 52. The computer 502 may include a system bus 508 may include any of several types of bus structures, including, for example, a memory bus or memory controller, a peripheral bus, and a local bus using any of a variety of conventional bus architectures such as peripheral component interconnect (PCI), video electronics standards association (VESA), Microchannel, industry standard architecture (ISA), and extended industry standard architecture (EISA), to name a few. The system memory 506 may include read only memory (ROM) 510 and/or random access memory (RAM) 512. A basic input/output system (BIOS), containing the basic routines that help to transfer information between elements within the computer 502, such as during start-up, may be stored in ROM 510.

The computer 502 also may include, for example, a hard disk drive 514, a magnetic disk drive 516 (e.g., a floppy drive), e.g., to read from or write to a removable disk 518, and an optical disk drive 520 (e.g., a CD-ROM drive), e.g., for reading from or writing to a CD-ROM disk 522 or other optical media. The hard disk drive 514, magnetic disk drive 516, and optical disk drive 520 are connected to the system bus 508 by a hard disk drive interface 524, a magnetic disk drive interface 526, and an optical disk drive interface 528, respectively. The drives and their associated computer-readable media provide nonvolatile storage of data, data structures, computer-executable instructions, etc. for the computer 502. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, may also be used in the exemplary operating environment 500, and further that any such media may contain computer-executable instructions for performing the methods of the invention, such as including the functions of the analysis engine 17 of FIG. 29 and associated methods and functions disclosed with respect to FIGS. 30-36.

A number of program modules may be stored in the drives and RAM 512, including an operating system 530, one or more application programs 532, other program modules 534, and program data 536. The operating system 530 in the computer 502 could be any suitable operating system or combinations of operating systems. The application programs 532, other program modules 534, and program data 536 can cooperate to provide motor and cognitive testing on a patient computer device, such as shown and described above. Additionally, application programs 532, other program modules 534, and program data 536 can be used for computation of an indication of motor, cognitive or a combination of motor and cognitive functions of a patient based on the testing data, such as shown and described above.

A user may enter commands and information into the computer 502 through one or more user input devices, such as a keyboard 538 and a pointing device (e.g., a mouse 540). Other input devices (not shown) may include a microphone, a joystick, a game pad, a scanner, touch screen, or the like. Other data (e.g., acceleration data and gyroscope data) 536 can be provided by still other input devices, such as sensors, via corresponding interfaces. In some examples, the accelerometer and the gyroscope can be co-located on a device (e.g., a smartphone, PDA or tablet computer) that is attached to or held by the user during administration of a test. The mouse or other pointing device can be utilized to perform a point-and-click action, which includes the action of a computer user moving a cursor to a certain location on a screen (point) and then pressing a mouse button, usually the left button (click), or other pointing device. Such point-and-click can be used with any number of input devices varying from mice, touch pads, keyboards, joysticks, scroll buttons, and roller balls. The information associated with such point and click operations can be provided (e.g., to a central server) as part of the test data (e.g., test data 30, 31 and 32) for each of the respective tests, such as described herein.

These and other input devices can be connected to a processing unit 504 through a serial port interface 542 that is coupled to the system bus 508, but may be connected by other interfaces, such as a parallel port, a game port or a universal serial bus (USB). A display device 544, such as a monitor, is also connected to the system bus 508 via an interface, such as a video adapter 546. Other display devices, such as speakers, printers, etc. may be provided instead of or in addition to the monitor. Thus, the output representation for a virtual electrode is not limited to a graphical representation on a display.

The computer 502 may operate in a networked environment using logical connections to one or more remote computers 560. The remote computer 560 may be a workstation, a server computer, a router, a peer device, or other common network node, and typically includes many or all of the elements described relative to the computer 502, although, for purposes of brevity, only a memory storage device 562 is illustrated in FIG. 28. The logical connections depicted in FIG. 28 may include a LAN 564 and/or a WAN 566. Such networking environments are commonplace in offices, enterprise-wide computer networks, intranets, and the Internet.

When used in a LAN networking environment, the computer 502 is connected to the LAN 564 through a network interface or adapter 568. When used in a WAN networking environment, the computer 502 typically includes a modem 570, or is connected to a communications server on an associated LAN, or has another circuitry arrangement for establishing communications over the WAN 566, such as the Internet. The modem 570, which may be internal or external, is connected to the system bus 508 via the serial port interface 542. In a networked environment, program modules depicted relative to the computer 502, or portions thereof, may be stored in the remote memory storage device 562 (and/or locally). It will be appreciated that the network connections shown are exemplary and other arrangements for establishing a communications link between the computers 502 and 560 may be used.

Example embodiments of systems and methods relating to the assessment of concussion-related functions will now be described. Concussion injuries are often difficult to evaluate because a comprehensive evaluation may require assessment of multiple functions. Thus, concussion generally requires a multi-factor approach involving a battery of tests, including tests for balance/postural stability.

Although described in connection with the assessment and treatment of traumatic brain injuries, the example systems and methods may also be applied to other types of medical conditions that affect the same functions as concussions. For example, the systems and methods may be used to assess and/or treat patients with balance or vestibular impairments or Parkinson's disease not caused by a concussion injury.

Analysis Engine

Figure 29:
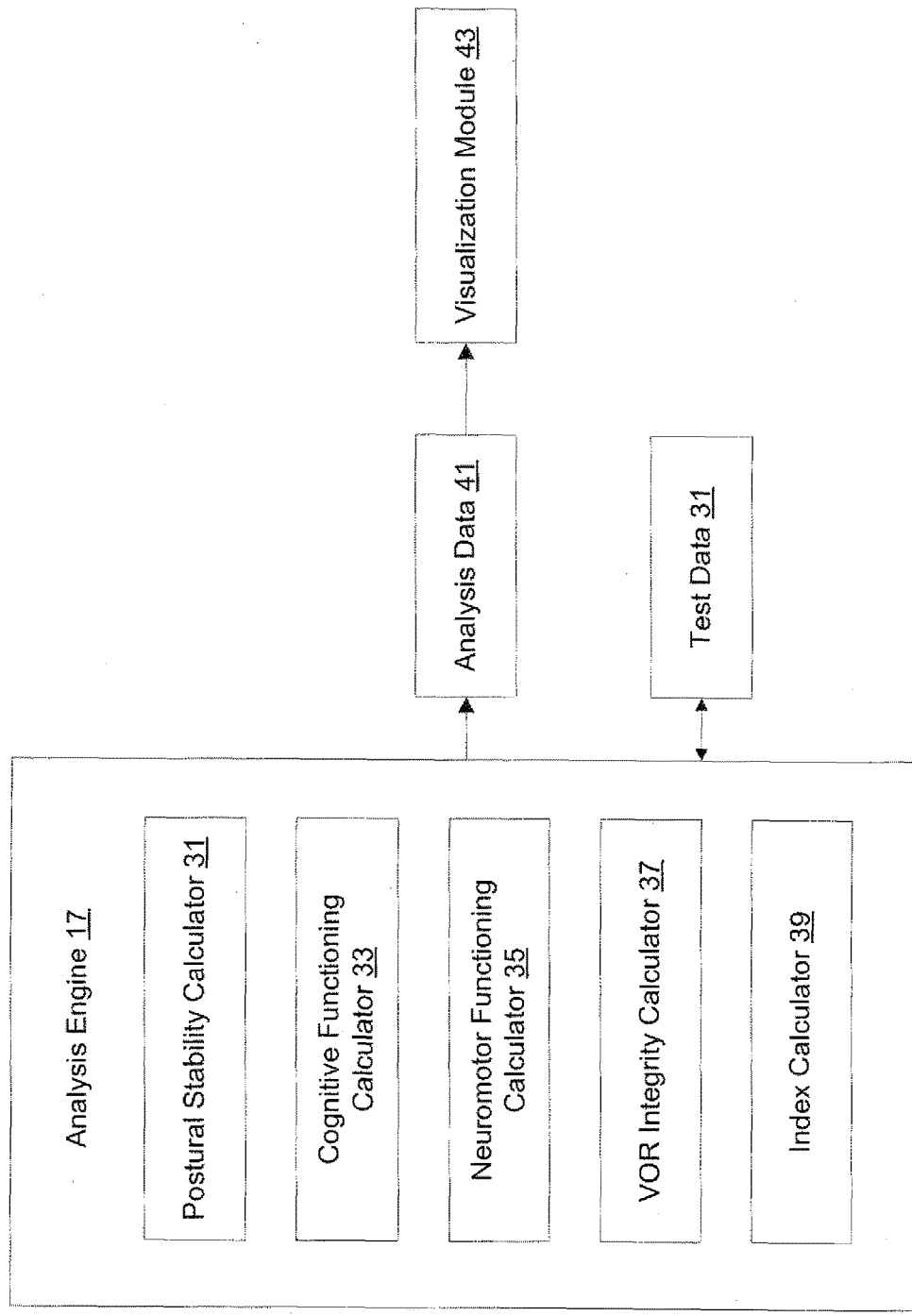
FIG. 29 is a block diagram of an analysis engine for a test and analysis system, according to an example embodiment of the invention.

FIG. 29 depicts an example of an analysis engine 16 that may be used as an alternative to the analysis engine 16 in FIG. 1. The analysis engine 16 may include at least one of a balance/postural stability calculator 31, a neuromotor functioning calculator 35, a VOR integrity calculator 37 and an index calculator 39. In other examples, the analysis engine can also include a cognitive functioning calculator 33. Each of the respective calculators can compute performance variables characterizing a respective function of the user based on test data, collectively demonstrated at 31, which can be stored in memory, such as can be obtained in response to user interactions with a device used to perform the test, such as disclosed herein. When implemented with the test engine 12 of FIG. 1, the test engine 12 may provide for concussion-related test data to be transmitted to or otherwise made accessible by the analysis engine 16 for analysis.

Concussion-related functions can broadly be defined as falling into one of four domains: cognitive, neuromotor, balance and postural stability, and vestibular. The cognitive domain may include functions such as memory/recall, information processing ability and set switching. The neuromotor domain may include reaction time and coordination. The balance and postural stability domain may include vision, somatosensory function and vestibular system function. The vestibular domain also relates to the vestibular system, but may specifically include VOR, vision and dizziness. The domains may have overlapping functions (e.g., vision is both a balance/postural stability function and a vestibular function). These four domains can also be utilized for evaluating other brain disorders, such as for example Parkinson's disease.

Each concussion-related function may be evaluated using one or more tests, the results of which can be stored in memory as the test data 31. Postural stability may be evaluated via accelerometer and/or gyroscope data, Balance Error Scoring System (BESS) testing and determining postural sway. Cognitive functioning may be evaluated using a Sport Concussion Assessment Tool (SCAT) test (which is a standard questionnaire test for concussion injuries) and testing working memory, set-switching or delayed recognition. Additionally or alternatively, cognitive functioning can be evaluated using one or more of a sevens test, a trail making test, a clock drawing test, a center-out test, an Archimedes spiral test, a judgment of line orientation test or the like, such as shown and disclosed herein in relation to FIGS. 1-27. Thus, the cognitive functioning can be evaluated according one or more of the cognitive testing and analysis approaches shown and described above.

VOR integrity may be evaluated by testing static visual acuity (e.g., asking the patient to indicate the orientation of an image while the patient remains stationary relative to the image), testing dynamic visual acuity (e.g., asking the patient to indicate the orientation of an image while the patient is moving relative to the image), and testing perception time. Neuromotor functioning may be evaluated by testing reaction time, such as disclosed herein. Examples of reaction time tests can include simple reaction time (SRT) and choice reaction time (CRT). For example, SRT may involve displaying an image and instructing the patient to press a button as soon as the image is displayed. CRT may involve displaying a image in one of a plurality of display locations (e.g., a left side or a right side of the display) and instructing the user to select the correct display location (e.g., touching the image when the image is displayed on a touch screen).

In an example embodiment of the invention, the calculators 31/33/35/37 are programmed to compute variables or parameters relevant to assessing the functions of their respective domains based on corresponding test data 17. For example, the postural stability calculator 31 may compute one or more BESS variables based on data from an administered BESS test and the neuromotor functioning calculator 35 may compute one or more variables relating to SRT or CRT, e.g., the duration between when a stimulus is displayed and when the patient inputs a valid response.

The index calculator 39 may be programmed to compute one or more indices (e.g., also referred to herein as scores) based upon the output results determined by each of the calculators 31/33/35/37 for a patient. For example, the index calculator 39 can aggregate the analysis data determined for a given set of test data acquired for a given patient to compute an index (or score) having a value indicative of postural stability for the given patient based on the aggregate set of test data (e.g., gyroscope data may be aggregated with accelerometer data to determine postural sway). Alternatively or additionally, the index calculator 39 can compute indices (or scores), each value of which is indicative of one of a BESS test (e.g., a BESS score), a SCAT or SCAT2 test (e.g., a SCAT score), working memory, set-switching, delayed recognition, static visual acuity, perception time, dynamic visual acuity, SRT or CRT. The resulting output for the index calculation can be provided and stored as part of analysis data 41 for subsequent analysis, e.g., by a clinician who may access the stored analysis data 41. The analysis data 41 may be input to a visualization module 43 for subsequent display, as described below.

Visualization Module

Concussion-related functions may be assessed prior to injury in order to establish a set of baseline metrics (e.g., scores or indices) for each patient. A post-injury assessment may be performed to generate a subsequent set of metrics that are then compared to the baseline metrics. In an example embodiment, the visualization module 43 may be configured to output instructions for displaying the baseline metrics in conjunction with displaying the subsequent set of metrics. Each set of metrics may be displayed as a spider graph, so that a spider graph corresponding to the subsequent set of metrics is superimposed onto a spider graph corresponding to the baseline metrics for simultaneous display. Alternatively, the visualization module can display simultaneously two or more respective spider graphs (e.g., side-by-side display of baseline and post-injury metrics).

Figure 30:
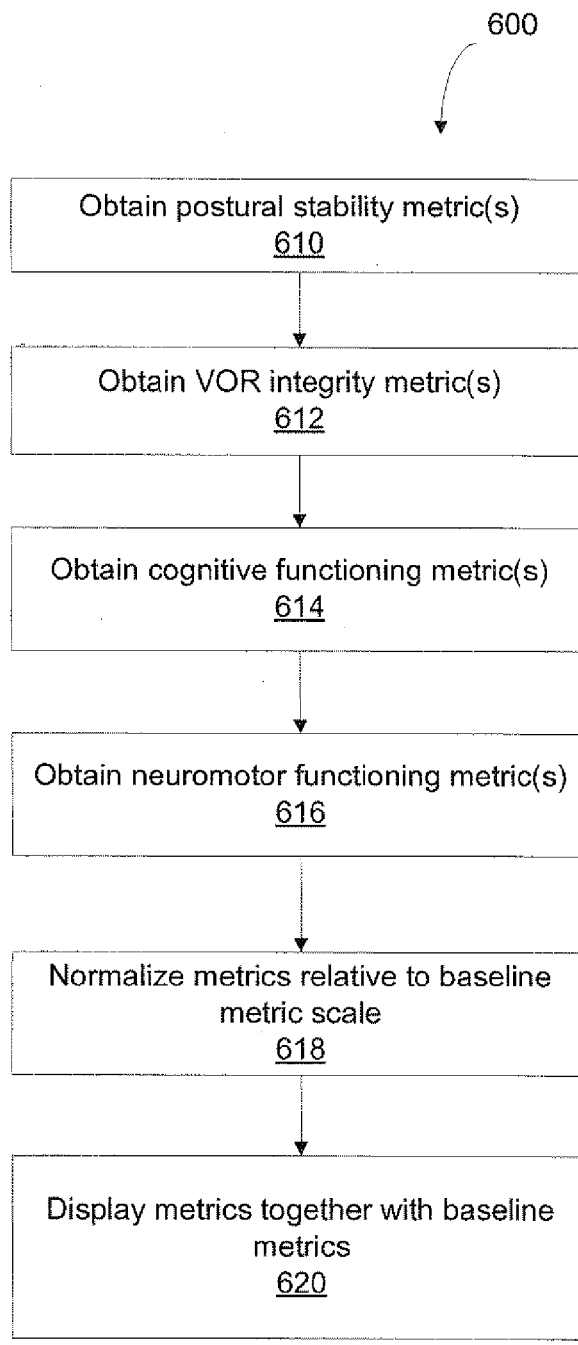
FIG. 30 is a flowchart that shows a method for displaying concussion-related performance metrics, according to an example embodiment of the invention.
Figure 31:
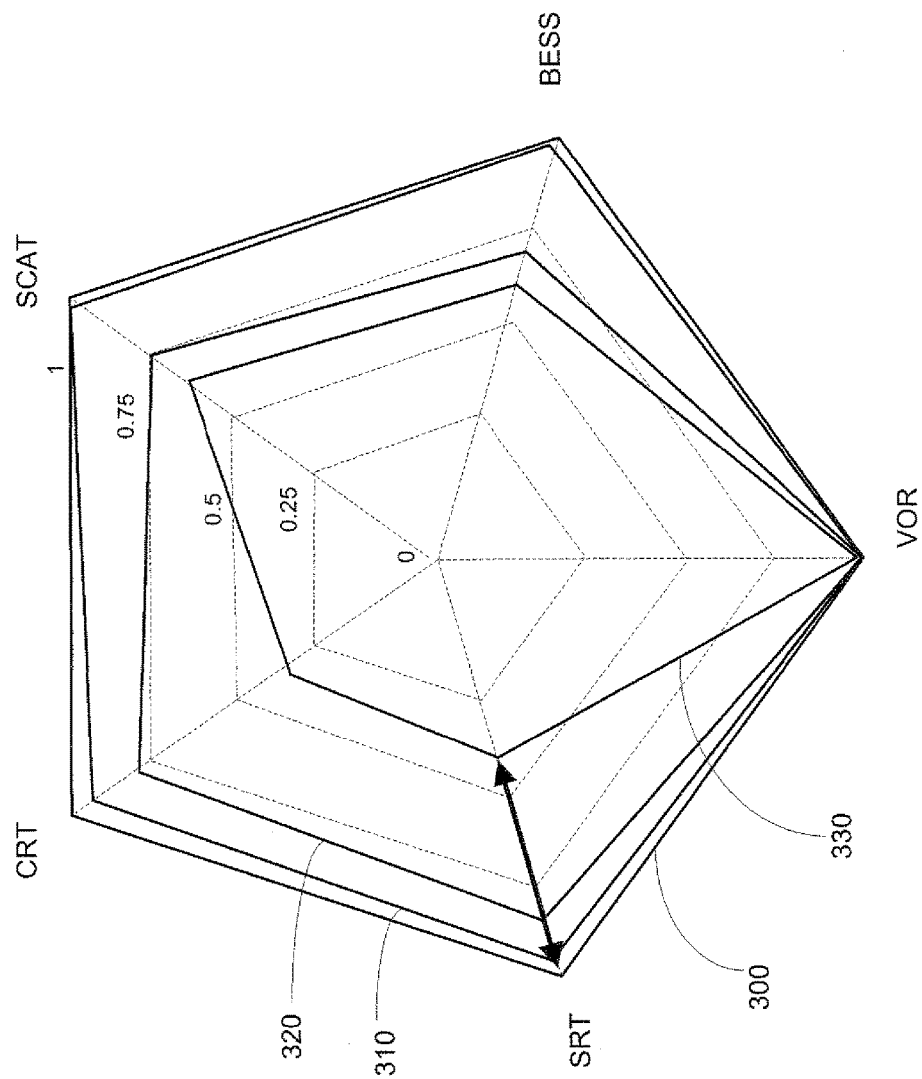
FIG. 31 is a set of spider graphs corresponding to example results from a series of tests performed on a first patient, according to an example embodiment of the invention.

The spider graphs may include any combination of scores and/or indices. For example, FIG. 31 shows spider graphs 300/310/320/330, the vertices of which include scores/indices for SRT, CRT, SCAT, BESS and VOR. Different numbers and indices can be utilized as vertices depending on the tests performed, including any of those disclosed herein, for example. The operation of the visualization module 43 is illustrated in FIG. 30, which is a flowchart showing a method 600 for displaying concussion-related performance metrics. The method 600 may be performed after obtaining a set of baseline metrics and begins at step 610, in which a subsequent postural stability metric(s) is obtained, e.g., from the analysis data 41. In an example embodiment of the invention, the method 600 obtains at least one metric from each concussion domain. Accordingly, in steps 612/614/616, metrics are obtained which respectively relate to VOR integrity, cognitive functioning and neuromotor functioning. For each baseline metric, a corresponding subsequent metric counterpart may be obtained.

At step 618, the subsequent metrics may be normalized relative to a baseline metric scale. According to an example embodiment, the baseline metrics correspond to a fully functional or normal state for the subject patient. The baseline metrics may also be scaled to facilitate visual understanding. For example, each baseline score or index can be considered as having a scaled value of 1 on a scale from 0 to 1. The visualization module 43 may compute a difference between the baseline metrics and their counterpart subsequent metrics, e.g., a percentage change relative to each respective baseline metric. The subsequent metrics are then scaled based on the difference. For example, a difference of 25% would, on a scale of 0 to 1, correspond to a scaled value of 0.75.

At step 620, the baseline metrics may be displayed together with the scaled subsequent metrics. The spider graphs shown in FIGS. 31 and 32 correspond to example displayed results for two different patients. Each patient was evaluated at several points in time, beginning with a baseline assessment (300/400), then an evaluation twenty-four hours after a concussion injury (310/410), an evaluation three days after the same injury (320/420) and an evaluation ten days after the same injury (330/430). Thus, any number of subsequent evaluations may be performed, each resulting in a new spider graph.

Figure 32:
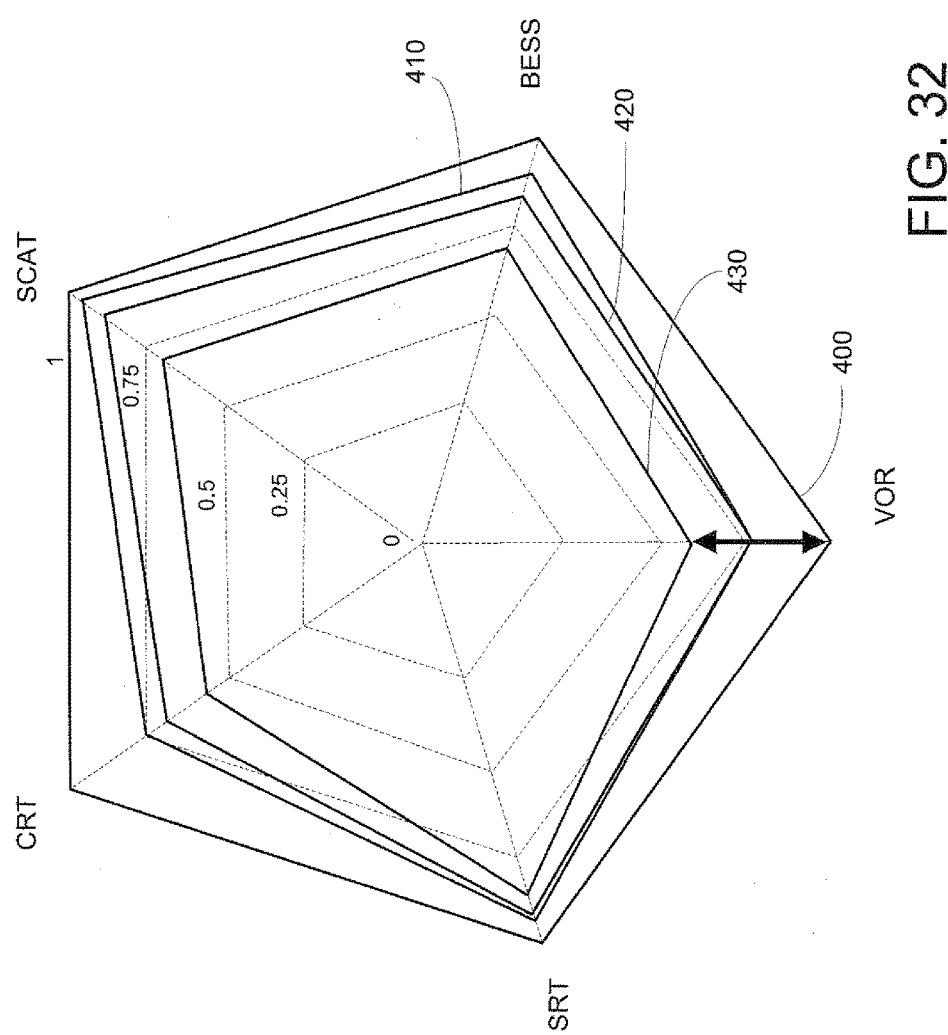
FIG. 32 is a set of spider graphs corresponding to example results from a series of tests performed on a second patient, according to an example embodiment of the invention.

As shown in the examples of FIGS. 31 and 32, each patient suffered a decrease in function following injury. An advantage of displaying the metrics in the form of a spider graph, and in particular a normalized spider graph, lies in that because each patient may respond differently to injury (e.g., different types of injury may affect different functions and each patient may respond to the same type of injury in a different way), the comparison of different patients is facilitated by simultaneously showing how each baseline metric changed relative to the individual patient so that, instead of comparing raw scores or indices of different patients, it may be easier to simply visualize how each patient has been affected relative to his or her own baseline. To illustrate this, the patient in FIG. 31 experienced substantial worsening of SRT and CRT after ten days (330), with moderate worsening of SCAT and BESS and almost no difference in VOR. In contrast, the patient in FIG. 32 experienced little worsening of SRT after ten days (430), but moderate worsening of CRT, SCAT, BESS and VOR.

Displaying the metrics in the manner described above may facilitate return-to-play decisions in sports, e.g., whether an injured player should resume playing can be dependent on a clinician's assessment of how impaired the player is relative to his baseline. Clinicians may have different opinions as to which metric is most important to a player's continued ability to play. For example, a clinician may value VOR over CRT, so that a substantial worsening of CRT may nonetheless result in an opinion that the player can continue to play, so long as VOR remains substantially the same. In addition to return-to-play decisions, the displaying of the metrics may also be useful in therapeutic interventions, e.g., in DBS, stimulation parameters may target specific functions, so that a worsening of VOR can be treated using a specific stimulation parameter combination different from a combination used to treat worsening of CRT.

Determining Postural Stability and VOR Integrity

In an example embodiment, postural stability may be determined using objective tests in addition, or as an alternative, to subjective tests such as BESS. While conventional BESS testing relies on the subjective interpretation of a test administrator (e.g., to determine whether the patient is in the correct stance), it may be desirable to include objective data for assessing postural stability. Accordingly, one example embodiment relates to combining data obtained from a gyroscope and an accelerometer. In a preferred embodiment, the gyroscope and accelerometer may be co-located in a single portable device, e.g., a device that is attached to or held by the user patient (e.g., a PDA, smartphone, tablet PC or the like). Additionally, this portable device may include a display (e.g., a touch screen) for administering at least one of the tests previously described, e.g., an SRT, CRT or trails test.

Figure 33:
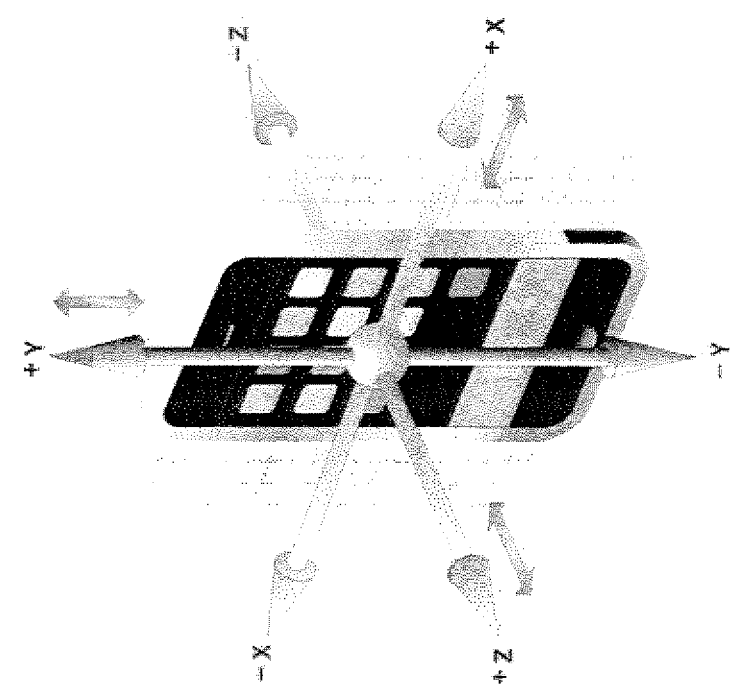
FIG. 33 depicts a set of measurements obtained using a conventional accelerometer.

FIG. 33 depicts a set of measurements obtained using a conventional accelerometer. In a three-axis coordinate system (e.g., xyz coordinates) the accelerometer is capable of measuring linear acceleration along any one of the three axes. Thus, for example, the accelerometer may provide information pertaining to changes in the position of the patient's body relative to the anterior, posterior, lateral or medial directions.

Figure 34:
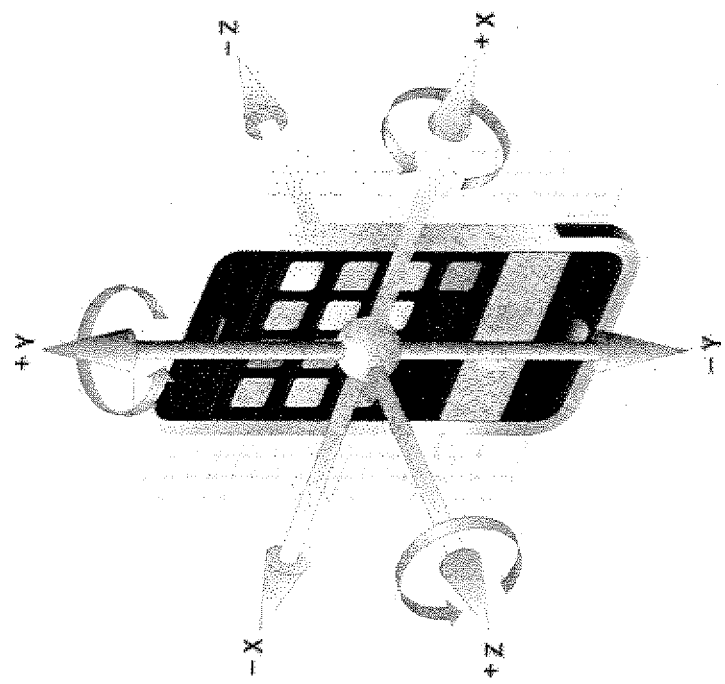
FIG. 34 depicts a set of measurements obtained using a conventional gyroscope.

FIG. 34 depicts a set of measurements obtained using a conventional gyroscope. In contrast to the accelerometer, the gyroscope provides information pertaining to angular rotation about any of the three axes. In an example embodiment, gyroscope measurements are used to supplement accelerometer measurements, providing more data about the patient's movements than an accelerometer alone.

Figure 35:
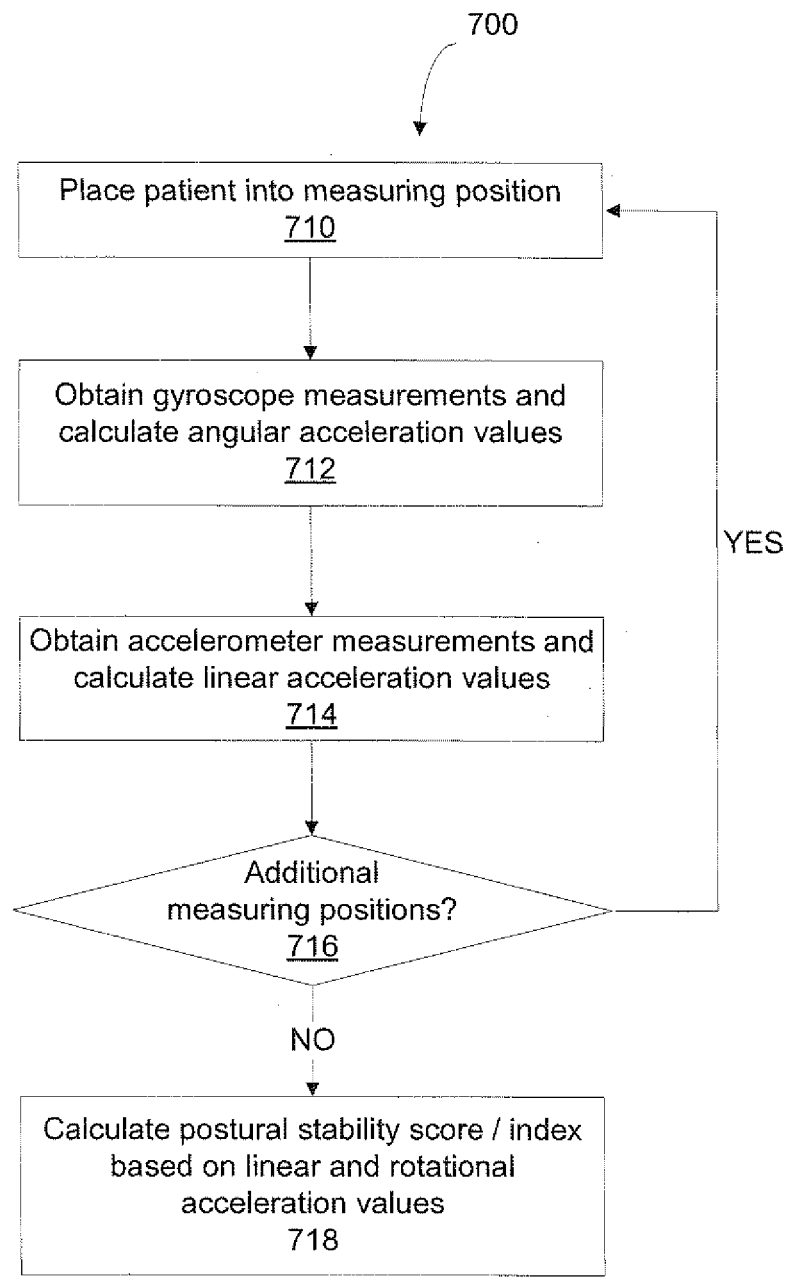
FIG. 35 is a flowchart that shows a method for determining postural stability based on combined gyroscope and accelerometer data.

FIG. 35 is a flowchart that shows a method 700 for determining postural stability based on combined gyroscope and accelerometer data. The method 700 may begin at step 710 by having the test administrator place the patient into a measuring position. The measuring position may be one of any number of conventional measuring positions, such as those used in BESS. For example, the patient may be asked to balance himself on a mat, which may or may not be inclined relative to the ground. The patient may be asked to maintain a balanced position for as long as possible. The patient may be asked to maintain the position which looking in a certain direction, at a distant target, or with eyes closed. Other variations in measuring position/condition are possible and would be known to one of ordinary skill in the art. The method 700 may be used alone to generate objective data measuring postural stability. Alternatively or additionally, the method 700 may be used to independently verify the accuracy of BESS test results.

In step 712, the gyroscope measurements are obtained and angular acceleration values calculated from those measurements. The calculation may be performed, e.g., using the analysis engine 17.

In step 714, the accelerometer measurements are obtained and linear acceleration values are calculated. The method 700 may then proceed to step 716, where it may be determined whether additional measuring positions or conditions are required. For example, the angle of inclination of the pad may be adjusted or the patient may be asked to change posture. If there are additional positions/conditions, the method 700 returns to step 710.

When no measuring positions or conditions are remaining, a postural stability score or index may be calculated based on the obtained measurements. Gyroscope and accelerometer data may be used to determine the location of the patient's center of gravity as a function of parameters that may include how fast, how far, and in what direction the user is moving. The calculation of center of gravity as a function of these parameters would be known to one of ordinary skill in the art.

Changes in the location of the center of gravity over time may be used to calculate a score or index for postural stability. For example, postural sway may be computed based on the average deviation for center of gravity, a function of the difference between the patient's initial center of gravity (e.g., when the accelerometer/gyroscope begins recording) and an average center of gravity location and/or a function of a frequency and/or severity of deviations from the initial center of gravity.

In an example embodiment, the functions of the vestibular system are tested and measured. For example, balance and postural stability are related to proper functioning of the vestibular system. VOR is also related to the vestibular system. In particular, when the patient is moving his head during a VOR test, the vestibular system operates to stabilize images to maintain visual acuity, help maintain postural stability, and to provide information for spatial orientation. These are accomplished in large part by the anatomic structures of the peripheral vestibular system and its neurophysiologic connections to the visual system and motor pathways.

The vestibular labyrinth includes anatomical structures that respond to changes in body position. Certain structures respond to linear acceleration, whereas other structures respond to angular acceleration. The accelerations are generated when the patient's body changes position. The anatomical structures react to the accelerations, and the continued ability of the patient to maintain balance or posture is a function of these reactions. The movement of the patient (e.g., in an attempt to maintain postural stability) generates further accelerations, which can then be measured using the gyroscope and/or accelerometer. For example, the semicircular canals, utricle, and saccule generate afferent information regarding spatial orientation to elicit balance reactions via connections with cerebellar and motor pathways to maintain postural stability.

In addition to reactions that relate to postural stability, visual reactions (e.g., pertaining to VOR) may occur. Afferent input from the vestibular organs may synapse with the oculomotor nerves to generate rapid compensatory eye movements to maintain visual focus. Common symptoms of vestibular dysfunction include dizziness, impaired balance, blurred vision, vertigo, and decreased tolerance of bright lights, noise, or movement. Such symptoms can be measured and detected using VOR and other visual tests.

Intentional Underperformance and Anticipation

Accurate testing of concussion-related functions depends on the cooperation of the patient. Athletes may have an incentive to underperform during baseline testing, so that during subsequent testing performed following injury, worsening in function may not appear as significant relative to baseline function.

Additionally, there may be occasions where a patient anticipates the correct response to a task or question during testing. For example, anticipation may result from a fortuitous guess as to the location of the next target when the next target has yet to be displayed. Anticipation may also result from cheating, including memorization of tasks such as a trail trajectory. Accordingly, it is desirable to detect intentional underperformance and anticipation.

Figure 36:
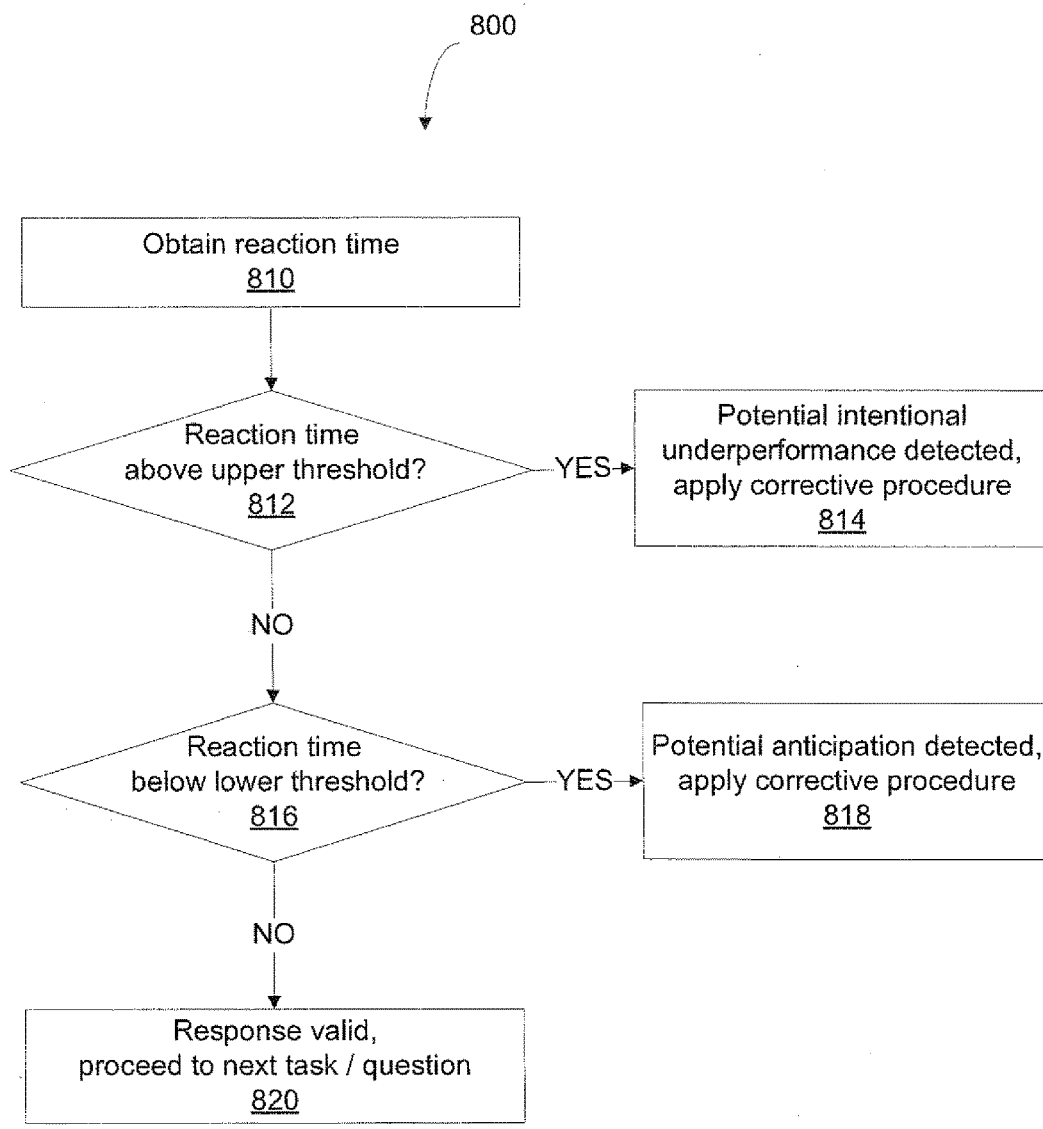
FIG. 36 is a flowchart that shows a method for detecting potential intentional underperformance and anticipation by a patient test-taker.

FIG. 36 is a flowchart that shows a method 800 for detecting potential intentional underperformance and anticipation by a patient test-taker. The method 800 may begin at 810, where the patient's reaction time (e.g., SRT or CRT) is obtained.

At step 812, it may be determined whether the reaction time is above an upper threshold. If the reaction time is above the upper threshold, this indicates potential intentional underperformance and the method proceeds to step 814, where a corrective procedure is performed. The corrective procedure may be as simple as ignoring (e.g., invalidating or deleting) the response associated with the reaction time. In an example embodiment, the corrective procedure may involve substituting the original task or question with a new task/question of equal difficulty. Alternatively, the difficulty level can be changed in order to gauge whether the patient is performing as expected in response to the change in difficulty. For example, it would be expected that a patient would take longer to respond to a task of higher difficulty. However, if the patient is intentionally underperforming, the patient may respond in substantially the same manner as before (e.g., take equally as long to respond). Alternatively, the original task may be repeated at a later time, e.g., after several additional tasks, in order to compare the reaction times of two or more instances of the original task.

If the upper threshold is not exceeded, the method may proceed to step 816, where it may be determined whether the reaction time is below a lower threshold, which would indicate potential anticipation and trigger another corrective procedure (step 818).

In an example embodiment, the upper and lower threshold values are obtained from statistics information pertaining to norms for similarly situated individuals, selected from among other patients or members of the general population. For example, upper and lower threshold values may be obtained by referencing reaction times of other patients having the same age as the subject patient. The upper threshold may correspond to an absolute maximum or average maximum reaction time observed among all patients of the same age as, or within an age range (e.g., plus or minus two years) of, the subject patient. Similarly, the lower threshold may correspond to an absolute minimum or average minimum observed reaction time among all patients of the same age or age range. Other clinical factors may be used for selecting the group of similarly situated individuals, including gender, height, weight, body mass index, body proportion (e.g., the length of the legs relative to the torso) and disease condition (e.g., Alzheimer's).

If the reaction time is not below the lower threshold, then neither anticipation nor intentional underperformance has been detected and the response is valid, and the method proceeds to the next task or question (820).

While the method 800 has been described in connection with the detection of intentional underperformance and anticipation during SRT and CRT testing, the method 800 may also be applied towards other types of tests that involve a timed response. For example, age-norm quality control may also be applied to postural stability (e.g., how quickly the patient changes position) and cognitive functioning tests (e.g., how quickly the patient recognizes a displayed object).

In accordance with the practices of persons skilled in the art of computer programming, the invention has been described with reference to acts and symbolic representations of operations that are performed by a computer, such as the computer 502 or remote computer 560, unless otherwise indicated. Such acts and operations are sometimes referred to as being computer-executed. It will be appreciated that the acts and symbolically represented operations include the manipulation by the processing unit 504 of electrical signals representing data bits which causes a resulting transformation or reduction of the electrical signal representation, and the maintenance of data bits at memory locations in the memory system (including the system memory 506, hard drive 514, floppy disks 518, CD-ROM 522, and remote memory storage 562) to thereby reconfigure or otherwise alter the computer system's operation, as well as other processing of signals, and/or store data obtained as results of such processing. The memory locations where such data bits are maintained are physical locations that have particular electrical, magnetic, or optical properties corresponding to the data bits.

What have been described above are examples and embodiments of the invention. It is, of course, not possible to describe every conceivable combination of components or methodologies for purposes of describing the invention, but one of ordinary skill in the art will recognize that many further combinations and permutations of the invention are possible. For example, the approach can be utilized to help diagnose other conditions or disorder than traumatic brain injury.

What is claimed is:
1. A system, comprising:
a tablet computer or a smartphone comprising an accelerometer, a gyroscope, a non-transitory memory, and a processor, wherein:
the accelerometer measures a linear acceleration of the tablet computer or the smartphone as a function of time during at least one test interval;
the gyroscope measures an angular rotation of the tablet computer or the smartphone as a function of time during the at least one test interval;
the non-transitory memory storing computer-executable instructions; and
the processor executes the computer-executable instructions to cause a computing device to at least:
retrieve a baseline postural stability score and a baseline vestibulo-ocular reflex (VOR) integrity score, wherein the baseline postural stability score and the baseline VOR integrity score are previously determined;
during a test period to assess balance and postural stability of a user using a balance and postural stability test conducted on the tablet computer or the smartphone during the at least one test interval, wherein the balance and postural stability are assessed based on (i) the linear acceleration of the tablet computer or the smartphone positioned on the user during the balance and postural stability test using the accelerometer and (ii) the angular rotation of the tablet computer or the smartphone positioned on the user during the balance and postural stability test using the gyroscope;
compute a dwell time representing a time interval from a first user task to a second user task during at least one of the test periods;
determine a postural stability score for the user based on changes in the linear acceleration and the angular rotation that occur over time during the balance and postural stability test and based on the computed dwell time
during another test period to assess vestibule-ocular reflex (VOR) integrity of the user using a VOR test conducted on the tablet computer or the smart phone, determine VOR integrity test data during the other test period;
determine a VOR integrity score for the user based on the vestibulo-ocular reflex (VOR) integrity test data for the user;
display a baseline spider graph comprising the baseline postural stability score and the baseline VOR integrity score; and
display another spider graph comprising the postural stability score and the VOR integrity score together with the baseline spider graph to facilitate monitoring of an extent of a given injury of the user.

2. The system of claim 1, wherein the another spider graph is overlaid on top of the baseline spider graph to facilitate the monitoring of the extent of the given injury of the user.

3. The system of claim 1, wherein the another spider graph and the baseline spider graph are displayed side-by-side to facilitate the monitoring of the extent of the given injury of the user.

4. The system of claim 1, wherein the processor executes the computer-executable instructions to normalize the postural stability score and the VOR integrity score with respect to the baseline postural stability score and the baseline VOR integrity score.

5. The system of claim 1, wherein the processor executes the computer-executable instructions to:
retrieve a baseline cognitive function score and a baseline neuromuscular function score;
retrieve cognitive function test performance data and neuromuscular function test performance data for the user;
determine a cognitive function score for the user based on the cognitive function test performance data; and
determine a neuromuscular function score for the user based on the neuromuscular function test performance data,
wherein the baseline spider graph further comprises the baseline cognitive function score and the baseline neuromuscular function score, and
wherein the another spider graph further comprises the cognitive function score and the neuromuscular function score.

6. The system of claim 1, wherein the postural stability score is related to a change in a location of a center of gravity of the user based on the linear acceleration value and the angular rotation value.

7. The system of claim 1, wherein the given injury of the user comprises one of a traumatic brain injury, multiple sclerosis, or Parkinson's disease.

8. A method, comprising:
retrieving, by a tablet computer or a smartphone comprising an accelerometer, a gyroscope, a non-transitory memory, and a processor, a baseline postural stability score and a baseline vestibulo-ocular reflex (VOR) integrity score, wherein the baseline postural stability score and the baseline VOR integrity score are previously determined;
administering, by the tablet computer or the smartphone, a test for balance and postural stability comprising:
measuring, by the accelerometer, a linear acceleration value for a user as a function time during a postural stability test to assess balance and postural stability of a user while the user holds or wears the tablet computer or the smartphone during the postural stability test;
measuring, by the gyroscope, an angular rotation value for the user as a function time during the postural stability test;
computing a dwell time representing a time interval from a first user task to a second user task during at least one test period; and
determining a postural stability score for the user based on changes in the linear acceleration value and the angular rotation value that occur over time during the postural stability test and based on the dwell time;
administering, by the tablet computer or the smartphone, a vestibulo-ocular reflex (VOR) integrity test to determine VOR integrity test data for the user;
determining, by the tablet computer or the smartphone, a VOR integrity score for the user based on the VOR integrity test data;
displaying, by the tablet computer or the smartphone, a baseline spider graph with vertices corresponding to the baseline postural stability score and the baseline VOR integrity score; and
displaying, by the tablet computer or the smartphone, another spider graph with vertices corresponding to the postural stability score and the VOR integrity score together with the baseline spider graph to facilitate monitoring of an extent of a given injury of the user.

9. The method of claim 8, wherein the other spider graph is overlaid on top of the baseline spider graph to facilitate the monitoring of the extent of the given injury of the user.

10. The method of claim 8, wherein the other spider graph and the baseline spider graph are displayed side-by-side to facilitate the monitoring of the extent of the given injury of the user.

11. The method of claim 8, further comprising normalizing the postural stability score and the VOR integrity score with respect to the baseline postural stability score and the baseline VOR integrity score.

12. The method of claim 8, further comprising:
retrieving a baseline cognitive function score and a baseline neuromuscular function score;
retrieving cognitive function test performance data and neuromuscular function test performance data for the user;
determining a cognitive function score for the user based on the cognitive function test performance data; and
determining a neuromuscular function score for the user based on the neuromuscular function test performance data,
wherein the baseline spider graph further comprises the baseline cognitive function score and the baseline neuromuscular function score, and
wherein the another spider graph further comprises the cognitive function score and the neuromuscular function score.

13. The method of claim 8, wherein the postural stability score is related to a change in a location of a center of gravity of the user based on the linear acceleration value and the angular rotation value.

14. The method of claim 8, wherein the given injury of the user comprises one of a traumatic brain injury, multiple sclerosis, or Parkinson's disease.

15. The method of claim 8, wherein the linear acceleration value, the angular rotation value, and the vestibulo-ocular reflex (VOR) integrity test data for a user each comprises an associated response time;
further comprising:
determining whether the linear acceleration value, the angular rotation value, or the VOR test data are associated with an intentional underperformance or an anticipatory response based on the associated response time.

16. The method of claim 15, wherein:
the intentional underperformance occurs when the associated response time is greater than an upper threshold; and
the anticipatory response occurs when the associated response time is less than a lower threshold.

17. The system of claim 1, wherein the processor executes the computer-executable instructions further to determine a measure of at least one of a motor function or cognitive function during the computed dwell time.

18. The method of claim 15, wherein in response to determining that at least one of the linear acceleration value, the angular rotation value or the VOR test data are associated with the intentional underperformance or the anticipatory response, the method further comprises modifying a difficulty of a subsequent test for the user.

* * * * *

UNITED STATES PATENT AND TRADEMARK OFFICE
CERTIFICATE OF CORRECTION

| | | |
|---|---|---|
| PATENT NO. | : 9,610,029 B2 | Page 1 of 1 |
| APPLICATION NO. | : 13/644371 | |
| DATED | : April 4, 2017 | |
| INVENTOR(S) | : Jay L. Alberts | |

It is certified that error appears in the above-identified patent and that said Letters Patent is hereby corrected as shown below:

In the Specification

Column 1, Line 19, please insert the following paragraph:
--GOVERNMENT FUNDING
This invention was made with government support under NS07317 awarded by the National Institutes of Health. The government has certain rights in the invention.--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*